US012741066B2

(12) United States Patent
Pindzola et al.

(10) Patent No.: US 12,741,066 B2
(45) Date of Patent: Sep. 22, 2026

(54) DEVICE FOR SUPPORTING SURGICAL PROCEDURES AND METHOD OF MANUFACTURE THEREOF

(71) Applicant: Triton Systems, Inc., Chelmsford, MA (US)

(72) Inventors: Brad Pindzola, Cambridge, MA (US); Lucas Rozanski, Chicopee, MA (US); Douglas Wich, Somerville, MA (US); Doris Möncke, Alfred, NY (US); Lucas Greiner, Rolla, MO (US)

(73) Assignee: Triton Systems, Inc., Chelmsford, MA (US)

( * ) Notice: Subject to any disclaimer, the term of this patent is extended or adjusted under 35 U.S.C. 154(b) by 0 days.

(21) Appl. No.: 18/944,384

(22) Filed: Nov. 12, 2024

(65) Prior Publication Data

US 2026/0131056 A1 May 14, 2026

(51) Int. Cl.

| | |
|---|---|
| ***A61L 31/12*** | (2006.01) |
| ***A61F 2/82*** | (2013.01) |
| ***A61L 31/14*** | (2006.01) |
| ***C03B 17/04*** | (2006.01) |

(52) U.S. Cl.

CPC ........... *A61L 31/123* (2013.01); *A61L 31/143* (2013.01); *A61F 2/82* (2013.01); *C03B 17/04* (2013.01)

(58) Field of Classification Search

CPC ........ A61L 31/123; A61L 31/143; A61F 2/82; C03B 17/04

See application file for complete search history.

(56) References Cited

U.S. PATENT DOCUMENTS

| | | | | |
|---|---|---|---|---|
| 2005/0169967 A1* | 8/2005 | Gilchrist | A61L 31/02 424/426 |
| 2006/0172877 A1* | 8/2006 | Fechner | A01N 59/16 501/48 |
| 2016/0120548 A1* | 5/2016 | Paul, Jr. | A61B 17/11 623/1.2 |

FOREIGN PATENT DOCUMENTS

| | | | |
|---|---|---|---|
| CN | 1328853 | A | 1/2002 |
| CN | 116002976 | A | 4/2023 |
| GB | 2178422 | A | 2/1987 |
| KR | 20210022399 | A | 3/2021 |
| WO | 1996031160 | A1 | 10/1996 |
| WO | 2015087069 | A1 | 6/2015 |
| WO | 2017013447 | A1 | 1/2017 |
| WO | 2024153929 | A1 | 7/2024 |

* cited by examiner

*Primary Examiner* — Michael C Miggins
(74) *Attorney, Agent, or Firm* — CALDWELL LLC

(57) ABSTRACT

A device for supporting surgical procedures and method of its manufacture include preparing a glass melt in a silica crucible, injecting a gas bubble into the glass melt, shaping the glass melt containing the gas bubble into a phosphate glass structure having a tubular shape, cooling the phosphate glass structure, wherein the phosphate glass structure includes a network-forming component and a modifier, and truncating the phosphate glass structure into a desired length to form the device, wherein the device has a dissolution rate of at least 50 mg $cm^{-2}$ $hr^{-1}$.

31 Claims, 6 Drawing Sheets

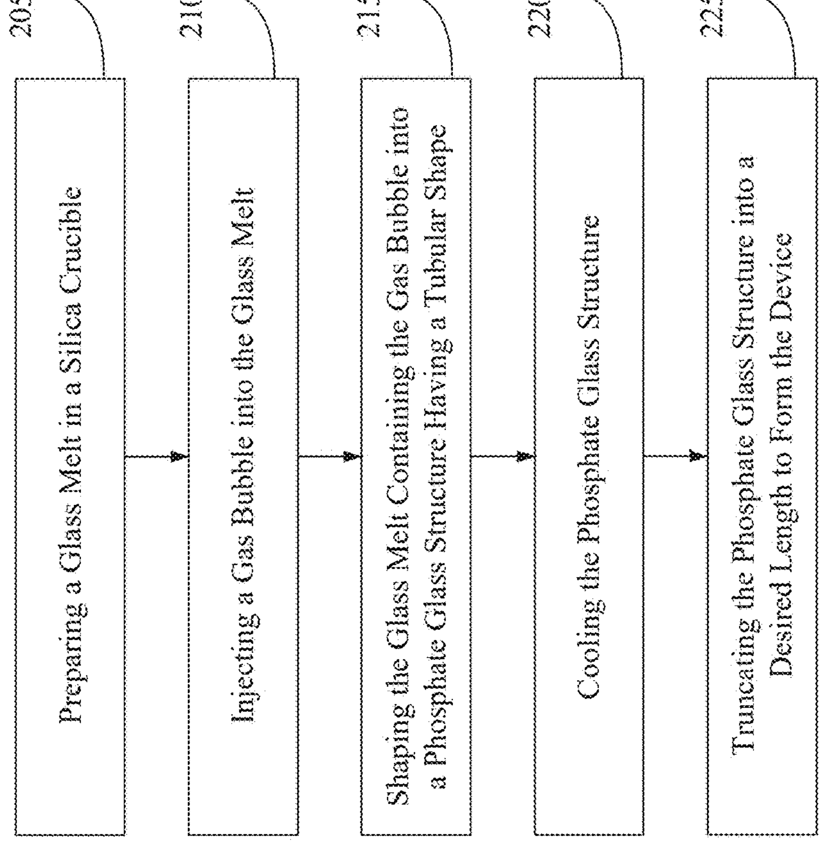
FIG. 2

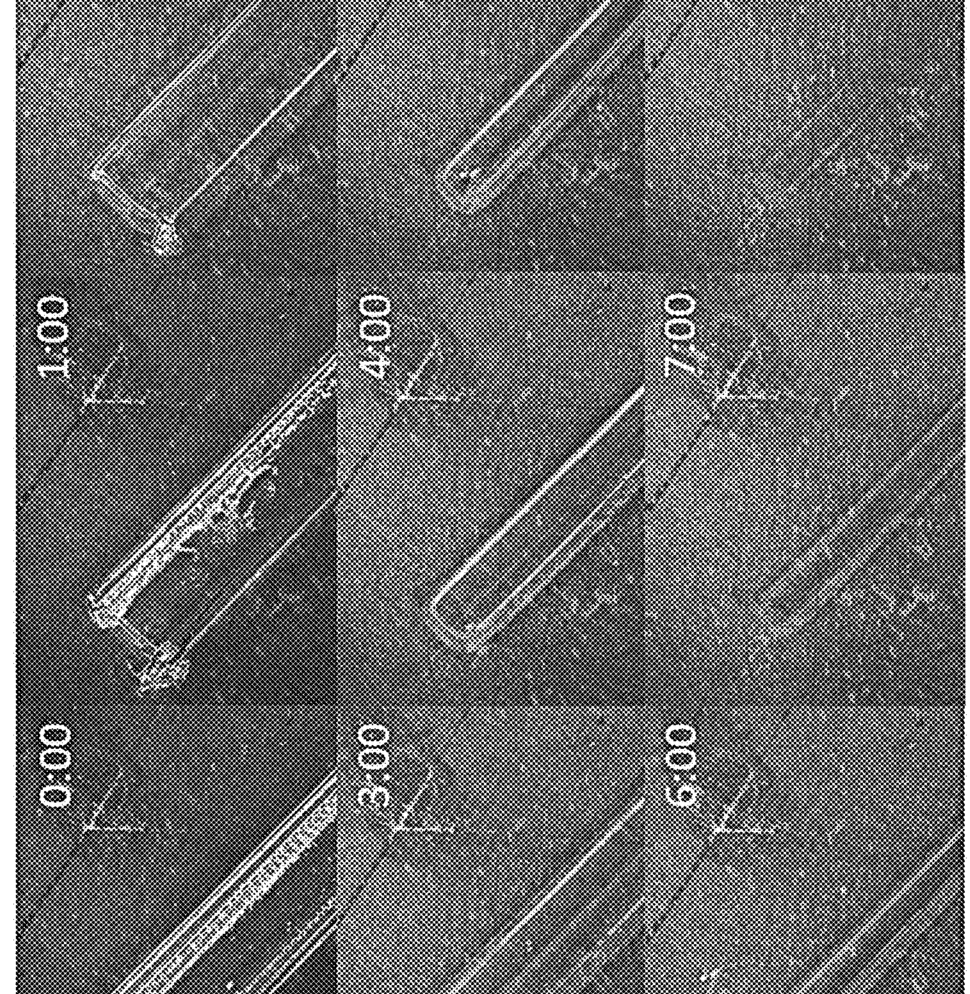
FIG. 3

400

500

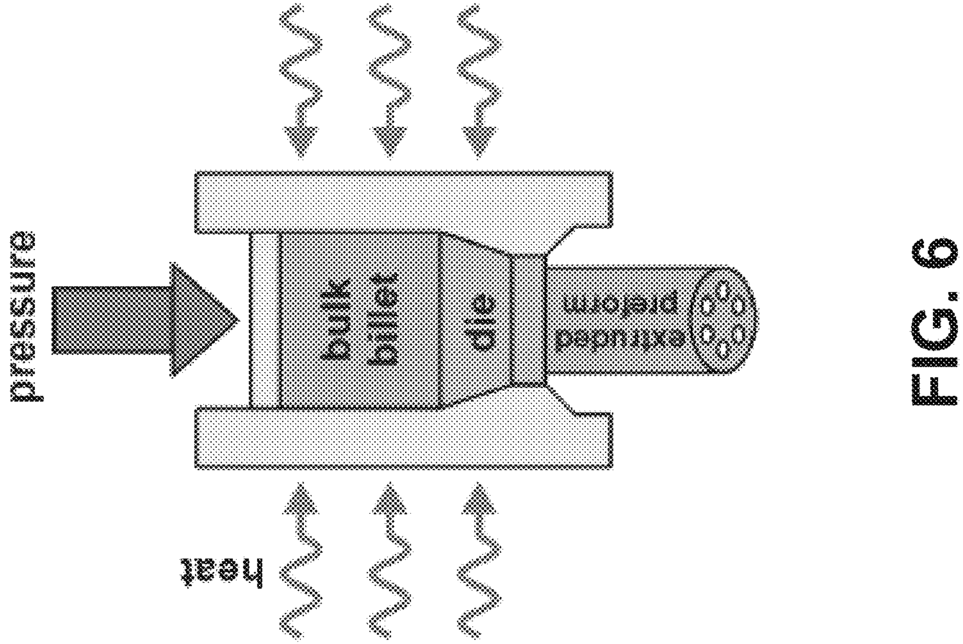
FIG. 6

DEVICE FOR SUPPORTING SURGICAL PROCEDURES AND METHOD OF MANUFACTURE THEREOF

STATEMENT OF GOVERNMENT SUPPORT

This invention was made with government support under Army Medical Research Acquisition Activity Contract HT9425-23-C-0012, awarded by the National Science Foundation. The government has certain rights in the invention.

FIELD OF THE INVENTION

The present invention generally relates to the field of medical devices. In particular, the present invention is directed toward devices for supporting surgical procedures and methods of manufacture thereof.

BACKGROUND

A surgical procedure such as wound closure, anastomosis, and/or the like, may benefit from the use of certain support structures such as scaffolds or stents. These support structures help bring surfaces into apposition, provide for a sufficient tissue overlap to create a strong bond therebetween, and minimize the risk of errors, such as without limitation having a needle pierce through an entire vessel. These support structures also help ensure that the lumen underneath a site of operation remains open and provide sufficient strength to avoid dehiscence. However, these support structures are often constructed using material or materials with a limited dissolution rate. As a result, they may remain inside a patient's body for an extended period, which may create long-term problems, such as without limitation stenosis due to a turbulence of blood flow. Additionally, some support structures may break down into one or more non-physiological, cytotoxic products and/or fragment into shards of foreign materials; these species may cause potential health and safety hazards when present in the blood stream. Support structures for medical procedures with fast, tunable dissolution rates, negligible cytotoxic effects, and satisfactorily low safety hazards do not yet exist.

SUMMARY OF THE DISCLOSURE

In an aspect, a device for supporting surgical procedures is described. The device includes a phosphate glass matrix having a tubular shape. The phosphate glass matrix includes a network-forming component and a modifier. The modifier includes at most 15 mol % of CaO with respect to the phosphate glass matrix. The device has a dissolution rate of at least 50 mg $cm^{-2}$ $hr^{-1}$.

In another aspect, a method manufacturing a device for supporting surgical procedures is described. The method includes preparing a glass melt in a silica crucible. The method further includes injecting a gas bubble into the glass melt. The method further includes shaping the glass melt containing the gas bubble into a phosphate glass structure having a tubular shape. The method further includes cooling the phosphate glass structure, wherein the phosphate glass structure includes a network-forming component and a modifier. The method further includes truncating the phosphate glass structure into a desired length to form the device, wherein the device has a dissolution rate of at least 50 mg $cm^{-2}$ $hr^{-1}$.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a schematic illustration of an exemplary method of manufacturing a device for supporting surgical procedures;

FIG. 3 includes stills from an exemplary timelapse sequence of a device dissolving in static phosphate buffered saline (PBS) under eight minutes;

FIG. 6 includes a schematic illustration of an exemplary embodiment of an extrusion system; and The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
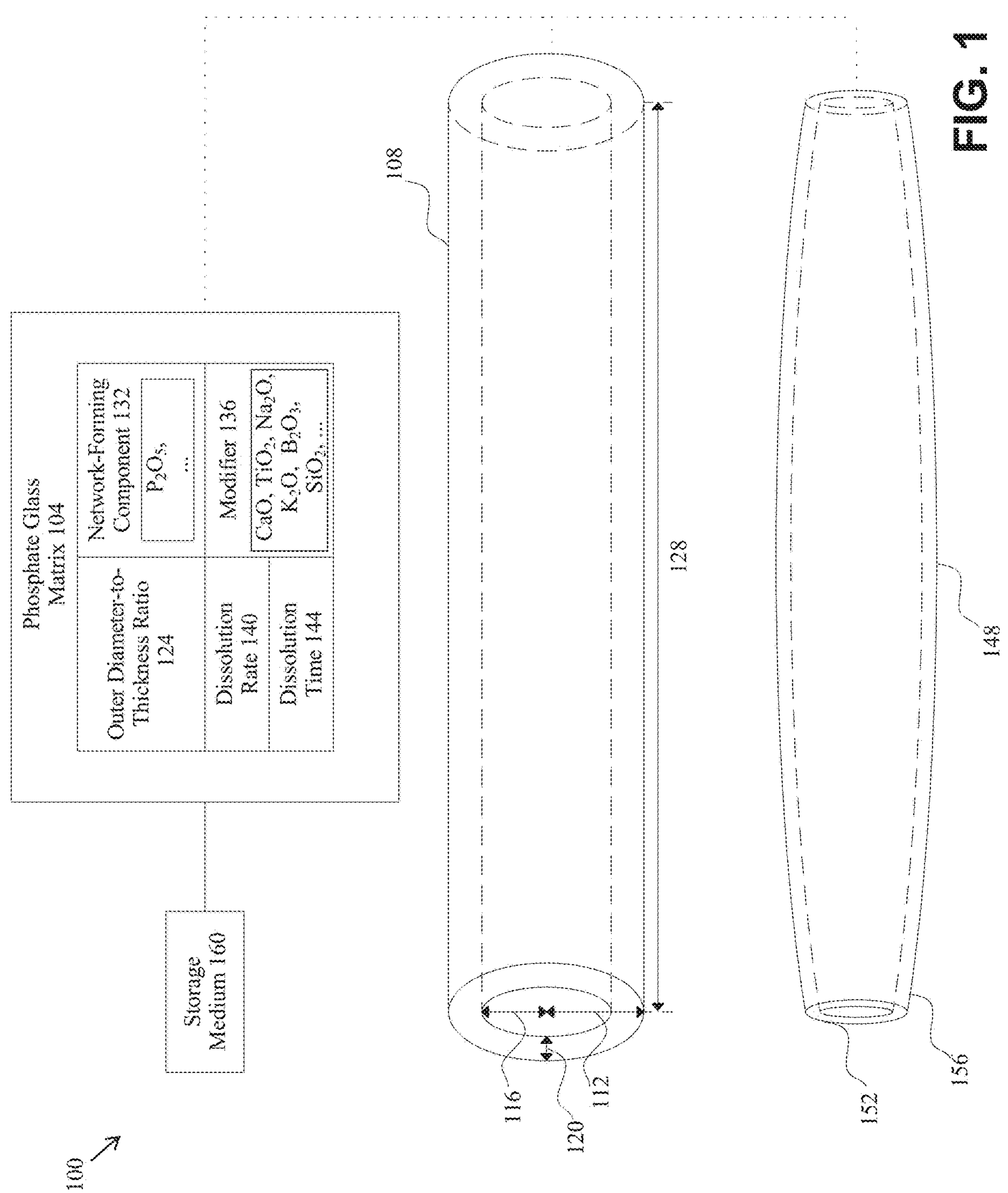
FIG. 1 is a schematic illustration of an exemplary embodiment of a device for supporting surgical procedures.

At a high level, aspects of the present disclosure are directed to a device for supporting surgical procedures and a method of manufacture thereof. The device includes a phosphate glass matrix having a tubular shape. In one or more embodiments, the tubular shape may have an outer diameter that is at least 1 millimeter and no greater than 5 millimeters. In some cases, the outer diameter may be at least 2 millimeters and no greater than 4 millimeters. More specifically, in some cases, the outer diameter may be at least 3.3 millimeters and no greater than 3.8 millimeters. In one or more embodiments, the tubular shape may have an outer diameter that is at least 1 centimeter and no greater than 10 centimeters. Specifically, tubular shape may have a diameter of about (e.g., +/−20%) 2.5 cm or 7.5 cm. In one or more embodiments, the tubular shape may have an outer diameter-to-thickness ratio that is at least 3 and no greater than 10. In some cases, the outer diameter-to-thickness ratio may be at least 4.5 and no greater than 5.5. More specifically, in some cases, the outer diameter-to-thickness ratio may be approximately 5. In one or more embodiments, the tubular shape may have a length that is at least 5 millimeters and no greater than 20 millimeters. In one or more embodiments, the tubular shape may further include one or more structural features such as without limitation a smooth outer surface, a smooth edge, and/or one or more tapered ends, among others.

The phosphate glass matrix includes a network-forming component. In one or more embodiments, the network-forming component may include at least 80 mol % and no greater than 95 mol % of $P_2O_5$ with respect to the phosphate glass matrix. In one or more embodiments, the network-forming component may include at least 45 mol % and no greater than 55 mol % of $P_2O_5$ with respect to the phosphate glass matrix. The phosphate glass matrix further includes a modifier. The modifier includes at most 15 mol % of CaO with respect to the phosphate glass matrix. In one or more embodiments, the modifier may further include at least 0.1 mol % and no greater than 5 mol % of $TiO_2$ with respect to the phosphate glass matrix. In one or more embodiments, the modifier may further include at least 0.1 mol % and no greater than 5 mol % of $SiO_2$ with respect to the phosphate glass matrix. In one or more embodiments, the modifier may further include at least 0.1 mol % and no greater than 5 mol % of $B_2O_3$ with respect to the phosphate glass matrix. In one or more embodiments, the modifier may further include at least 15 mol % and no greater than 30 mol % of $Na_2O$ with respect to the phosphate glass matrix. In one or more embodiments, the modifier may further include at least 15 mol % and no greater than 30 mol % of $K_2O$ with respect to the phosphate glass matrix. In one or more embodiments, when the network-forming component includes at least 80 mol % and no greater than 95 mol % of $P_2O_5$ with respect to the phosphate glass matrix, the phosphate glass matrix may have a glass melting temperature that is at least 400° C. and no greater than 600° C. In one or more embodiments, when the network-forming component includes at least 45 mol % and no greater than 55 mol % of $P_2O_5$ with respect to the phosphate glass matrix, the phosphate glass matrix may have a glass melting temperature that is at least 1,000° C. and no greater than 1,200° C.

In one or more embodiments, the device may be manufactured from a glass melt in a silica crucible. In some cases, the glass melt may be prepared from a mixture of precursors. The mixture may include chemicals such as without limitation $(NH_4)_3PO_4$, $CaCO_3$, $Na_2HPO_4$, and/or the like.

The device has a dissolution rate of at least 50 mg $cm^{-2}$ $hr^{-1}$. In one or more embodiments, the device may be configured to dissolve into physiological ions with negligible cytotoxic effects instead of fragmenting into pieces of foreign materials. In one or more embodiments, the device may have a dissolution time that is at least 2 minutes and no greater than 30 minutes.

In one or more embodiments, the device may further include a volume of storage medium within which the phosphate glass matrix is submerged. In some cases, the storage medium may include a neat nonaqueous, organic, and/or otherwise less polar solvent such as without limitation neat ethanol, neat isopropanol, or the like. In some other cases, the storage medium may include a moisture-free, gas-phase storage medium such as without limitation dry air, dry nitrogen, dry argon, or the like.

A method of manufacturing a device for supporting surgical procedures includes preparing a glass melt in a silica crucible. In one or more embodiments, preparing the glass melt may include preparing the glass melt from a mixture of precursors. The mixture may include chemicals such as without limitation $(NH_4)_3PO_4$, $CaCO_3$, $Na_2HPO_4$, and/or the like.

The method further includes injecting a gas bubble into the glass melt. The method further includes shaping the glass melt containing the gas bubble into a phosphate glass structure having a tubular shape. In one or more embodiments, shaping the glass melt may include extruding the glass melt using an extruder. In one or more embodiments, shaping the glass melt may further include shaping the glass melt into a tubular shape to create one or more structural features such as without limitation a smooth outer surface, a smooth edge, and one or more tapered ends, among others.

The method further includes cooling the phosphate glass structure. The method further includes truncating the phosphate glass structure into a desired length to form the device. In one or more embodiments, the method may further include submerging the device in a volume of storage medium.

Aspects of the present disclosure can be used as fast-dissolving scaffolds or stents in surgical procedures, such as without imitation wound closure and anastomosis. Aspects of the present disclosure may help reduce the health and safety hazards of absorbable or self-dissolving medical devices. Exemplary embodiments illustrating aspects of the present disclosure are described below in the context of several specific examples.

It is to be understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (e.g., a step is performed by or with the assistance of a human).

For the purposes of this disclosure, including the claims, the phrase "at least some" means "one or more" and includes the case of only one. Thus, e.g., the phrase "at least some ABCs" means "one or more ABCs" and includes the case of only one ABC.

For the purposes of this disclosure, including the claims, the term "at least one" should be understood as meaning "one or more" and therefore includes both embodiments that include one or multiple components. Furthermore, dependent claims that refer to independent claims that describe features with "at least one" have the same meaning, both when the feature is referred to as "the" and "the at least one".

For the purposes of this disclosure, the term "portion" means some or all. Therefore, for example, "A portion of X" may include some of "X" or all of "X". In the context of a conversation, the term "portion" means some or all of the conversation.

For the purposes of this disclosure, including the claims, the phrase "using" means "using at least" and is not exclusive. Thus, e.g., the phrase "using X" means "using at least X". Unless specifically stated by use of the word "only", the phrase "using X" does not mean "using only X".

For the purposes of this disclosure, including the claims, the phrase "based on" means "based in part on" or "based, at least in part, on" and is not exclusive. Thus, e.g., the phrase "based on factor X" means "based in part on factor X" or "based, at least in part, on factor X". Unless specifically stated by use of the word "only", the phrase "based on X" does not mean "based only on X".

In general, for the purposes of this disclosure, including the claims, unless the word "only" is specifically used in a phrase, it should not be read into that phrase.

For the purposes of this disclosure, including the claims, the phrase "distinct" means "at least partially distinct". Unless specifically stated, distinct does not mean fully distinct. Thus, e.g., the phrase “X is distinct from Y” means that “X is at least partially distinct from Y” and does not mean that “X is fully distinct from Y”. Thus, for the purposes of this disclosure, including the claims, the phrase “X is distinct from Y” means that X differs from Y in at least some way.

It should be appreciated that the words “first”, “second”, and so on, in the description and claims, are used to distinguish or identify, and not to show a serial or numerical limitation.

Similarly, letter labels (e.g., “(A)”, “(B)”, “(C)”, and so on, or “(a)”, “(b)”, and so on) and/or numbers (e.g., “(i)”, “(ii)”, and so on) are used to assist in readability and to help distinguish or identify, and are not intended to be otherwise limiting or to impose or imply any serial or numerical limitations or orderings. Similarly, words such as “particular”, “specific”, “certain”, and “given”, in the description and claims, if used, are to distinguish or identify, and are not intended to be otherwise limiting.

For the purposes of this disclosure, including the claims, the terms “multiple” and “plurality” mean “two or more,” and include the case of “two”. Thus, e.g., the phrase “multiple ABCs” means “two or more ABCs” and includes “two ABCs”. Similarly, e.g., the phrase “multiple PQRs” means “two or more PQRs” and includes “two PQRs”.

The present invention also covers the exact terms, features, values, and ranges, etc., in case these terms, features, values, and ranges, etc., are used in conjunction with terms such as “about”, “around”, “generally”, “substantially”, “essentially”, “at least”, etc. Thus, e.g., “about 3” or “approximately 3” shall also cover exactly 3, and “substantially constant” shall also cover exactly constant. Similarly, a numerical range “from X to Y” is intended to include both X and Y.

For the purposes of this disclosure, unless stated otherwise, the terms “about” or “approximately” refer to a value that is within 10% above or below the value being described.

For the purposes of this disclosure, including the claims, singular forms of terms are to be construed as also including the plural form and vice versa, unless the context indicates otherwise. Thus, it should be noted that for the purposes of this disclosure, the singular forms “a”, “an”, and “the” include plural references unless the context clearly dictates otherwise. In other words, terms such as “a”, “an”, and “the” are not intended to refer to only a singular entity but include the general class of which a specific example may be used for illustration.

Throughout the description and claims, the terms “comprise”, “including”, “having”, “contain”, and their variations should be understood as meaning “including but not limited to” and are not intended to exclude other components unless specifically so stated.

It is worth noting that the chemical formulas described in this disclosure may not necessarily represent true molecular formulae. Instead, in some cases, these chemical formulas may represent the empirical formulae of a chemical composition based on a simplified whole-number ratio between the number of each atom or ion. In some cases, the actual ratio between the number of atoms or ions may deviate from its expected stoichiometric ratio due to the presence of vacancies or enriched species, which may be introduced during synthesis or via post-synthetic processing; these cases, while not explicitly described in this disclosure, are still within the scope of this disclosure without limitation. In some cases, a chemical formula may only represent the chemical formula of a reactant without considering the composition of the final product.

It will be appreciated that variations to the embodiments of the invention can be made while still falling within the scope of the invention. Alternative features serving the same, equivalent, or similar purpose can replace features disclosed in the specification, unless stated otherwise. Thus, unless stated otherwise, each feature disclosed represents one example of a generic series of equivalent or similar features.

Use of exemplary language, such as “for instance”, “such as”, “for example” (“e.g.,”), and the like, is merely intended to better illustrate the invention and does not indicate a limitation on the scope of the invention unless specifically so claimed.

While the invention has been described in connection with what is presently considered to be the most practical and embodiments thereof are further described in the examples below, it is to be understood that the invention is not to be limited to the disclosed embodiment, but on the contrary, is intended to cover various modifications and equivalent arrangements included within the spirit and scope of the appended claims.

The following description sets forth various examples along with specific details to provide a thorough understanding of the claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Referring now to FIG. 1, an exemplary embodiment of a device 100 for supporting surgical procedures is illustrated. Device 100 includes a phosphate glass matrix 104. For the purposes of this disclosure, a “phosphate glass matrix” is a discrete unit or piece of phosphate glass. For the purposes of this disclosure, a “phosphate glass” is a class of amorphous materials containing phosphorus pentoxide ($P_2O_5$). In phosphate glass, $PO_4$ units form a glass network through covalent bonding, creating a unique type of glass with distinct chemical and thermal properties compared to silicate-based glasses. Certain modifiers may be added to phosphate glass in order to fine-tune its chemical properties, as described in further detail below. Phosphate glass is often characterized by its low melting point, high optical transparency, and high thermal expansion coefficient. Phosphate glass may be used in biomedical applications such as without limitation bioactive glasses for bone regeneration. Phosphate glass may also be used in optical fibers and specialty optics, lasers, and optical amplifiers. $P_2O_5$ is an acidic oxide and may react with water to form acidic, water-soluble species such as $H_3PO_4$. Therefore, by adjusting the mole fraction of $P_2O_5$, phosphate glass matrix 104 may be configured to dissolve at a range of tunable rates, as described in further detail below.

With continued reference to FIG. 1, device 100 is capable of dissolving in water or an aqueous solution, such as without limitation bodily fluid. Since an extended presence of device 100 within a patient’s body may lead to adverse long-term effects, such as without limitation stenosis due to a turbulence in blood flow, it is generally advantageous to engineer the composition of device 100 so that it dissolves at a relatively fast rate upon the completion of a medical procedure, e.g., once the blood flow is restored. For the purposes of this disclosure, "stenosis" is a medical condition characterized by an abnormal narrowing or constriction of a tubular structure or passage in the body. This narrowing may restrict the normal flow of fluids, air, or neural signals through the affected area, potentially causing significant physiological impairment. Stenosis may occur at blood vessels, airways, spinal canals, or gastrointestinal tracts, among other locations. However, it is worth noting that a rapid dissolution of phosphate glass matrix 104 may pose additional challenges to storing and handling device 100, as phosphate glass matrix 104 may become very moisture sensitive under such a condition. A rapid generation of acidic species such as $H_3PO_4$ inside a patient's body may also cause adverse biological effects, as certain proteins such as enzymes may denature when the pH of its solvent medium becomes too acidic. As a result, the mole fraction of $P_2O_5$ and the composition of phosphate glass matrix 104 should be carefully engineered to factor in and balance these considerations.

With continued reference to FIG. 1, phosphate glass matrix 104 has a tubular shape 108. For the purposes of this disclosure, a "tubular shape" is a three-dimensional geometry that contains a hollow center. A tubular shape may be characterized by a longitudinal axis that extends between its two distal ends and one or more lateral axes that extend within one or more of its cross-sections. Tubular shape 108 may include any elongated, hollow geometry deemed relevant to device 100 by a person of ordinary skill in the art, upon reviewing the entirety of this disclosure. In one or more embodiments, tubular shape 108 may include a cylindrical tube shape, an elliptical tube shape, a truncated ellipsoid shape, or the like. Tubular shape 108 may include one or more outer diameters 112 and one or more inner diameters 116, depending on whether the tubular shape 108 has a uniform cross-section along its longitudinal axis. For the purposes of this disclosure, an "outer diameter" is the diameter measured based on a cross-sectional area of the exterior of tubular shape 108. Similarly, for the purposes of this disclosure, an "inner diameter" is the diameter measured based on a cross-sectional area of the interior of tubular shape 108. When the cross-sectional area has a circular shape, outer diameter 112 and/or inner diameter 116 may refer to the diameter of the circle. Alternatively, when the cross-sectional area has an elliptical shape, outer diameter 112 and/or inner diameter 116 may refer to the major axis of the ellipse. Accordingly, tubular shape 108 may include one or more thicknesses 120, depending on the whether the thickness is uniform across the longitudinal axis. For the purposes of this disclosure, a "thickness" is a distance between the exterior surface and the interior surface of tubular shape 108. In one or more embodiments, thickness 120 may be at least 0.2 millimeter and no greater than 1 millimeter. As nonlimiting examples, thickness 120 may be from 0.2 millimeter to 0.3 millimeter, from 0.3 millimeter to 0.4 millimeter, from 0.4 millimeter to 0.5 millimeter, from 0.5 millimeter to 0.6 millimeter, from 0.6 millimeter to 0.7 millimeter, from 0.7 millimeter to 0.8 millimeter, from 0.8 millimeter to 0.9 millimeter, or from 0.9 millimeter to 1 millimeter, among others. As further nonlimiting examples, thickness 120 may be approximately 0.2 millimeter, approximately 0.3 millimeter, approximately 0.4 millimeter, approximately 0.5 millimeter, approximately 0.6 millimeter, approximately 0.7 millimeter, approximately 0.8 millimeter, approximately 0.9 millimeter, or approximately 1 millimeter, among others.

With continued reference to FIG. 1, in one or more embodiments, outer diameter 112 of tubular shape 108 may be at least 1 millimeter and no greater than 5 millimeters. Such an outer diameter range may be particular suitable for surgical procedures performed on a blood vessel. In some cases, outer diameter 112 may be at least 2 millimeters and no greater than 4 millimeters. More specifically, in some cases, the outer diameter may be at least 3.3 millimeters and no greater than 3.8 millimeters. As nonlimiting examples, outer diameter 112 may be from 1 millimeter to 2 millimeters, from 2 millimeters to 3 millimeters, from 3 millimeters to 3.1 millimeters, from 3.1 millimeters to 3.2 millimeters, from 3.2 millimeters to 3.3 millimeters, from 3.3 millimeters to 3.4 millimeters, from 3.4 millimeters to 3.5 millimeters, from 3.5 millimeters to 3.6 millimeters, from 3.6 millimeters to 3.7 millimeters, from 3.7 millimeters to 3.8 millimeters, from 3.8 millimeters to 3.9 millimeters, from 3.9 millimeters to 4 millimeters, or from 4 millimeters to 5 millimeters, among others. As further nonlimiting examples, outer diameter 112 may be approximately 1 millimeter, approximately 2 millimeters, approximately 3 millimeters, approximately 3.1 millimeters, approximately 3.2 millimeters, approximately 3.3 millimeters, approximately 3.4 millimeters, approximately 3.5 millimeters, approximately 3.6 millimeters, approximately 3.7 millimeters, approximately 3.8 millimeters, approximately 3.9 millimeters, approximately 4 millimeters, approximately 5 millimeters, approximately 6 millimeters, approximately 7 millimeters, approximately 8 millimeters, approximately 9 millimeters, or approximately 10 millimeters, among others.

With continued reference to FIG. 1, in one or more embodiments, outer diameter 112 of tubular shape 108 may be at least 1 centimeter and no greater than 10 centimeters. Such an outer diameter range may be particularly suitable for surgical procedures performed on an intestinal tract. For reference, the diameter of a small intestine in a human is approximately 2.5 centimeters (1 inch), while the diameter of a large intestine in a human is around 7.6 centimeters (3 inches). As nonlimiting examples, outer diameter 112 may be from 1 centimeter to 2 centimeters, from 2 centimeters to 3 centimeters, from 3 centimeters to 4 centimeters, from 4 centimeters to 5 centimeters, from 5 centimeters to 6 centimeters, from 6 centimeters to 7 centimeters, from 7 centimeters to 8 centimeters, from 8 centimeters to 9 centimeters, or from 9 centimeters to 10 centimeters, among others. As further nonlimiting examples, outer diameter 112 may be approximately 1 centimeter, approximately 2 centimeters, approximately 3 centimeters, approximately 4 centimeters, approximately 5 centimeters, approximately 6 centimeters, approximately 7 centimeters, approximately 8 centimeters, approximately 9 centimeters, or approximately 10 centimeters, among others. In such cases, thickness 120 of tubular shape 108 may be increased accordingly to maintain a desired mechanical strength of device 100.

With continued reference to FIG. 1, in one or more embodiments, tubular shape 108 may have an outer diameter-to-thickness ratio 124 that is at least 3 and no greater than 10. For the purposes of this disclosure, an "outer diameter-to-thickness ratio" is the ratio between outer diameter 112 and thickness 120 at a particular location of tubular shape 108. Since either outer diameter 112 or thickness 120 may vary along the longitudinal axis of tubular shape 108, outer diameter-to-thickness ratio 124 may also vary depending on the exact location sampled along the tubular shape 108. As nonlimiting examples, outer diameter-to-thickness ratio 124 may be from 3 to 4, from 4 to 5, from 5 to 6, from 6 to 7, from 7 to 8, from 8 to 9, or from 9 to 10, among others. As further nonlimiting examples, outer diameter-to-thickness ratio 124 may be approximately 3, approximately 4, approximately 5, approximately 6, approximately 7, approximately 8, approximately 9, or approximately 10, among others. In some cases, outer diameter-to-thickness ratio 124 may be at least 4.5 and no greater than 5.5.

With continued reference to FIG. 1, in one or more embodiments, tubular shape 108 may have a length 128 that is at least 5 millimeters and no greater than 20 millimeters. For the purposes of this disclosure, a "length" of tubular shape 108 is the dimension of the tubular shape 108 along its longitudinal axis, as described above. As nonlimiting examples, length 128 may be from 5 millimeters to 6 millimeters, from 6 millimeters to 7 millimeters, from 7 millimeters to 8 millimeters, from 8 millimeters to 9 millimeters, from 9 millimeters to 10 millimeters, from 10 millimeters to 11 millimeters, from 11 millimeters to 12 millimeters, from 12 millimeters to 13 millimeters, from 13 millimeters to 14 millimeters, from 14 millimeters to 15 millimeters, from 15 millimeters to 16 millimeters, from 16 millimeters to 17 millimeters, from 17 millimeters to 18 millimeters, from 18 millimeters to 19 millimeters, or from 19 millimeters to 20 millimeters, among others. As further nonlimiting examples, length 128 may be approximately 5 millimeters, approximately 6 millimeters, approximately 7 millimeters, approximately 8 millimeters, approximately 9 millimeters, approximately 10 millimeters, approximately 11 millimeters, approximately 12 millimeters, approximately 13 millimeters, approximately 14 millimeters, approximately 15 millimeters, approximately 16 millimeters, approximately 17 millimeters, approximately 18 millimeters, approximately 19 millimeters, or approximately 20 millimeters, among others. In some cases where outer diameter 112 is larger (e.g., 1 centimeter to 10 centimeters), as described above, length 128 may also be scaled up accordingly to maintain the mechanical strength and/or maneuverability of device 100. As nonlimiting examples, length 128 may be from 5 centimeters to 6 centimeters, from 6 centimeters to 7 centimeters, from 7 centimeters to 8 centimeters, from 8 centimeters to 9 centimeters, from 9 centimeters to 10 centimeters, from 10 centimeters to 11 centimeters, from 11 centimeters to 12 centimeters, from 12 centimeters to 13 centimeters, from 13 centimeters to 14 centimeters, from 14 centimeters to 15 centimeters, from 15 centimeters to 16 centimeters, from 16 centimeters to 17 centimeters, from 17 centimeters to 18 centimeters, from 18 centimeters to 19 centimeters, or from 19 centimeters to 20 centimeters, among others. As further nonlimiting examples, length 128 may be approximately 5 centimeters, approximately 6 centimeters, approximately 7 centimeters, approximately 8 centimeters, approximately 9 centimeters, approximately 10 centimeters, approximately 11 centimeters, approximately 12 centimeters, approximately 13 centimeters, approximately 14 centimeters, approximately 15 centimeters, approximately 16 centimeters, approximately 17 centimeters, approximately 18 centimeters, approximately 19 centimeters, or approximately 20 centimeters, among others.

With continued reference to FIG. 1, in one or more embodiments, tubular shape 108 may further include one or more structural features such as without limitation a smooth outer surface, a smooth edge, and/or one or more tapered ends, among others. These features, either in singularity or in combination, may facilitate the insertion, manipulation, movement, or the like, of device 100 when it is applied to a surgical procedure, such as without limitation anastomosis of blood vessels.

With continued reference to FIG. 1, phosphate glass matrix 104 includes a network-forming component 132. For the purposes of this disclosure, a "network-forming component" is a component that contains an extended network of chemical bonds that supports the overall integrity of a chemical composition. A network-forming component may be considered the structural pillar of a glass matrix and often imparts a certain extent of rigidity to the glass matrix. Accordingly, the extended network of chemical bonds within a network-forming component may include or adopt any type of topology, including without limitation linear, branched, star-shaped, among others, as recognized by a person of ordinary skill in the art, upon reviewing the entirety of this disclosure. Specifically, for phosphate glass matrix 104, network-forming component 132 includes extended chains of tetrahedral $PO_4$ units connected through the oxygen atoms at their vertices. Certain cations such as $Na^+$, $K^+$, $Ca^{2+}$, or the like may occupy the interstices of these extended chains to maintain charge balance, and these cations may be introduced via addition of one or more modifiers, as described in further detail below.

With continued reference to FIG. 1, in one or more embodiments, network-forming component 132 may include at least 80 mol % and no greater than 95 mol % of $P_2O_5$ with respect to phosphate glass matrix 104. As nonlimiting examples, network-forming component 132 may include from 80 mol % to 82 mol % of $P_2O_5$, from 82 mol % to 84 mol % of $P_2O_5$, from 84 mol % to 86 mol % of $P_2O_5$, from 86 mol % to 88 mol % of $P_2O_5$, from 88 mol % to 89 mol % of $P_2O_5$, from 89 mol % to 90 mol % of $P_2O_5$, from 90 mol % to 91 mol % of $P_2O_5$, from 91 mol % to 92 mol % of $P_2O_5$, from 92 mol % to 94 mol % of $P_2O_5$, or from 94 mol % to 95 mol % of $P_2O_5$ with respect to phosphate glass matrix 104, among others. As further nonlimiting examples, network-forming component 132 may include approximately 80 mol % of $P_2O_5$, approximately 82 mol % of $P_2O_5$, approximately 84 mol % of $P_2O_5$, approximately 86 mol % of $P_2O_5$, approximately 88 mol % of $P_2O_5$, approximately 89 mol % of $P_2O_5$, approximately 90 mol % of $P_2O_5$, approximately 91 mol % of $P_2O_5$, approximately 92 mol % of $P_2O_5$, approximately 94 mol % of $P_2O_5$, or approximately 95 mol % of $P_2O_5$ with respect to phosphate glass matrix 104, among others.

With continued reference to FIG. 1, in one or more embodiments, network-forming component 132 may include at least 45 mol % and no greater than 55 mol % of $P_2O_5$ with respect to phosphate glass matrix 104. As nonlimiting examples, network-forming component 132 may include from 45 mol % to 46 mol % of $P_2O_5$, from 46 mol % to 47 mol % of $P_2O_5$, from 47 mol % to 48 mol % of $P_2O_5$, from 48 mol % to 49 mol % of $P_2O_5$, from 49 mol % to 50 mol % of $P_2O_5$, from 50 mol % to 51 mol % of $P_2O_5$, from 51 mol % to 52 mol % of $P_2O_5$, from 52 mol % to 53 mol % of $P_2O_5$, from 53 mol % to 54 mol % of $P_2O_5$, or from 54 mol % to 55 mol % of $P_2O_5$ with respect to phosphate glass matrix 104, among others. As further nonlimiting examples, network-forming component 132 may include approximately 45 mol % of $P_2O_5$, approximately 46 mol % of $P_2O_5$, approximately 47 mol % of $P_2O_5$, approximately 48 mol % of $P_2O_5$, approximately 49 mol % of $P_2O_5$, approximately 50 mol % of $P_2O_5$, approximately 51 mol % of $P_2O_5$, approximately 52 mol % of $P_2O_5$, approximately 53 mol % of $P_2O_5$, approximately 54 mol % of $P_2O_5$, or approximately 55 mol % of $P_2O_5$ with respect to phosphate glass matrix 104, among others.

With continued reference to FIG. 1, phosphate glass matrix 104 further includes a modifier 136. For the purposes of this disclosure, a "modifier" is a chemical component that, upon mixing with network-forming component 132, affects (e.g., fine-tunes) a physical and/or chemical properties of phosphate glass matrix 104. Modifier 136 may include metallic atoms, clusters, or nanoparticles such as without limitation gold (Au), silver (Ag), and/or platinum (Pt). Modifier 136 may include metal oxides such as without limitation alkali metal oxides ($Li_2O$, $Na_2O$, $K_2O$, $Rb_2O$, and/or $Cs_2O$), alkaline earth metal oxides (BeO, MgO, CaO, SrO, and/or BaO), $Al_2O_3$, $TiO_2$, and/or the like. Modifier 136 may include nonmetal oxides such as without limitation $B_2O_3$, $SiO_2$, and/or the like. In one or more embodiments, certain modifiers 136, such as without limitation MgO and/or CaO, contain highly charged species (e.g., $Mg^{2+}$ and/or $Ca^{2+}$) that strengthen the ionic bonds within phosphate glass matrix 104. As a result, phosphate glass matrix 104 may show a superior strength and stability at room temperature and/or within an ambient environment. However, such modifiers 136 may also significantly increase the glass melting temperature required for manufacturing phosphate glass matrix 104, making it more challenging to shape and process. In one or more embodiments, certain modifiers 136 may contain one or more basic oxides, such as without limitation one or more alkali metal oxides and/or alkaline earth metal oxides. These basic oxides may react with water to generate basic species, such as, without limitation, alkali metal hydroxides and/or alkaline earth metal hydroxides. As a result, these basic oxides may counteract $P_2O_5$, which is an acidic oxide, as described above, and prevent device 100 from significantly acidifying a solvent medium (e.g., a blood stream) upon its dissolution. In one or more embodiments, certain modifiers 136, such as without limitation $B_2O_3$, may be used to lower the glass melting temperature of phosphate glass matrix 104 and/or increase the resistance of the phosphate glass matrix 104 against thermal shock. Additional details will be provided below in this disclosure. It is worth noting that the designation of network-forming component vs. modifier 136 in this disclosure may sometimes be arbitrary. As a nonlimiting example, in a context different from the present disclosure, $B_2O_3$ may itself function as a network-forming component for borate glass.

With continued reference to FIG. 1, modifier 136 includes at most 15 mol % of CaO with respect to phosphate glass matrix 104. As nonlimiting examples, modifier 136 may include from 0.001 mol % to 1 mol % of CaO, from 0.001 mol % to 1 mol % of CaO, from 1 mol % to 2 mol % of CaO, from 2 mol % to 3 mol % of CaO, from 3 mol % to 4 mol % of CaO, from 4 mol % to 5 mol % of CaO, from 5 mol % to 6 mol % of CaO, from 6 mol % to 7 mol % of CaO, from 7 mol % to 8 mol % of CaO, from 8 mol % to 9 mol % of CaO, from 9 mol % to 10 mol % of CaO, from 10 mol % to 11 mol % of CaO, from 11 mol % to 12 mol % of CaO, from 12 mol % to 13 mol % of CaO, from 13 mol % to 14 mol % of CaO, or from 14 mol % to 15 mol % of CaO with respect to phosphate glass matrix 104, among others. As further nonlimiting examples, modifier 136 may include approximately 0.001 mol % CaO, approximately 0.1 mol % CaO, approximately 1 mol % CaO, approximately 2 mol % CaO, approximately 3 mol % CaO, approximately 4 mol % CaO, approximately 5 mol % CaO, approximately 6 mol % CaO, approximately 7 mol % CaO, approximately 8 mol % CaO, approximately 9 mol % CaO, approximately 10 mol % CaO, approximately 11 mol % CaO, approximately 12 mol % CaO, approximately 13 mol % CaO, approximately 14 mol % CaO, or approximately 15 mol % CaO with respect to phosphate glass matrix 104, among others.

With continued reference to FIG. 1, in one or more embodiments, modifier 136 may further include at least 0.1 mol % and no greater than 5 mol % of $TiO_2$ with respect to phosphate glass matrix 104. As nonlimiting examples, modifier 136 may include from 0.1 mol % to 0.5 mol % of $TiO_2$, from 0.5 mol % to 1 mol % of $TiO_2$, from 1 mol % to 2 mol % of $TiO_2$, from 2 mol % to 3 mol % of $TiO_2$, from 3 mol % to 4 mol % of $TiO_2$, or from 4 mol % to 5 mol % of $TiO_2$ with respect to phosphate glass matrix 104. As further nonlimiting examples, modifier 136 may include approximately 0.1 mol % of $TiO_2$, approximately 0.5 mol % of $TiO_2$, approximately 1 mol % of $TiO_2$, approximately 2 mol % of $TiO_2$, approximately 3 mol % of $TiO_2$, approximately 4 mol % of $TiO_2$, or approximately 5 mol % of $TiO_2$ with respect to phosphate glass matrix 104.

With continued reference to FIG. 1, in one or more embodiments, modifier 136 may further include at least 0.1 mol % and no greater than 5 mol % of $SiO_2$ with respect to phosphate glass matrix 104. As nonlimiting examples, modifier 136 may include from 0.1 mol % to 0.5 mol % of $SiO_2$, from 0.5 mol % to 1 mol % of $SiO_2$, from 1 mol % to 2 mol % of $SiO_2$, from 2 mol % to 3 mol % of $SiO_2$, from 3 mol % to 4 mol % of $SiO_2$, or from 4 mol % to 5 mol % of $SiO_2$ with respect to phosphate glass matrix 104. As further nonlimiting examples, modifier 136 may include approximately 0.1 mol % of $SiO_2$, approximately 0.5 mol % of $SiO_2$, approximately 1 mol % of $SiO_2$, approximately 2 mol % of $SiO_2$, approximately 3 mol % of $SiO_2$, approximately 4 mol % of $SiO_2$, or approximately 5 mol % of $SiO_2$ with respect to phosphate glass matrix 104.

With continued reference to FIG. 1, in one or more embodiments, modifier 136 may further include at least 0.1 mol % and no greater than 5 mol % of $B_2O_3$ with respect to phosphate glass matrix 104. As nonlimiting examples, modifier 136 may include from 0.1 mol % to 0.5 mol % of $B_2O_3$, from 0.5 mol % to 1 mol % of $B_2O_3$, from 1 mol % to 2 mol % of $B_2O_3$, from 2 mol % to 3 mol % of $B_2O_3$, from 3 mol % to 4 mol % of $B_2O_3$, or from 4 mol % to 5 mol % of $B_2O_3$ with respect to phosphate glass matrix 104. As further nonlimiting examples, modifier 136 may include approximately 0.1 mol % of $B_2O_3$, approximately 0.5 mol % of $B_2O_3$, approximately 1 mol % of $B_2O_3$, approximately 2 mol % of $B_2O_3$, approximately 3 mol % of $B_2O_3$, approximately 4 mol % of $B_2O_3$, or approximately 5 mol % of $B_2O_3$ with respect to phosphate glass matrix 104.

With continued reference to FIG. 1, in one or more embodiments, modifier 136 may further include at least 15 mol % and no greater than 30 mol % of $Na_2O$ with respect to phosphate glass matrix 104. As nonlimiting examples, modifier 136 may include from 15 mol % to 16 mol % of $Na_2O$, from 16 mol % to 17 mol % of $Na_2O$, from 17 mol % to 18 mol % of $Na_2O$, from 18 mol % to 19 mol % of $Na_2O$, from 19 mol % to 20 mol % of $Na_2O$, from 20 mol % to 21 mol % of $Na_2O$, from 21 mol % to 21.5 mol % of $Na_2O$, from 21.5 mol % to 22 mol % of $Na_2O$, from 22 mol % to 22.5 mol % of $Na_2O$, from 22.5 mol % to 23 mol % of $Na_2O$, from 23 mol % to 23.5 mol % of $Na_2O$, from 23.5 mol % to 24 mol % of $Na_2O$, from 24 mol % to 25 mol % of $Na_2O$, from 25 mol % to 26 mol % of $Na_2O$, from 26 mol % to 27 mol % of $Na_2O$, from 27 mol % to 28 mol % of $Na_2O$, from 28 mol % to 29 mol % of $Na_2O$, or from 29 mol % to 30 mol % of $Na_2O$, among others. As further nonlimiting examples, modifier 136 may include approximately 15 mol % of $Na_2O$, approximately 16 mol % of $Na_2O$, approximately 17 mol % of $Na_2O$, approximately 18 mol % of $Na_2O$, approximately 19 mol % of $Na_2O$, approximately 20 mol % of $Na_2O$, approximately 21 mol % of $Na_2O$, approximately 21.5 mol % of $Na_2O$, approximately 22 mol % of $Na_2O$, approximately 22.5 mol % of $Na_2O$, approximately 23 mol % of $Na_2O$, approximately 23.5 mol % of $Na_2O$, approximately 24 mol % of $Na_2O$, approximately 25 mol % of $Na_2O$, approximately 26 mol % of $Na_2O$, approximately 27 mol % of $Na_2O$, approximately 28 mol % of $Na_2O$, approximately 29 mol % of $Na_2O$, or approximately 30 mol % of $Na_2O$, among others.

With continued reference to FIG. 1, in one or more embodiments, modifier 136 may further include at least 15 mol % and no greater than 30 mol % of $K_2O$ with respect to phosphate glass matrix 104. As nonlimiting examples, modifier 136 may include from 15 mol % to 16 mol % of $K_2O$, from 16 mol % to 17 mol % of $K_2O$, from 17 mol % to 18 mol % of $K_2O$, from 18 mol % to 19 mol % of $K_2O$, from 19 mol % to 20 mol % of $K_2O$, from 20 mol % to 21 mol % of $K_2O$, from 21 mol % to 21.5 mol % of $K_2O$, from 21.5 mol % to 22 mol % of $K_2O$, from 22 mol % to 22.5 mol % of $K_2O$, from 22.5 mol % to 23 mol % of $K_2O$, from 23 mol % to 23.5 mol % of $K_2O$, from 23.5 mol % to 24 mol % of $K_2O$, from 24 mol % to 25 mol % of $K_2O$, from 25 mol % to 26 mol % of $K_2O$, from 26 mol % to 27 mol % of $K_2O$, from 27 mol % to 28 mol % of $K_2O$, from 28 mol % to 29 mol % of $K_2O$, or from 29 mol % to 30 mol % of $K_2O$, among others. As further nonlimiting examples, modifier 136 may include approximately 15 mol % of $K_2O$, approximately 16 mol % of $K_2O$, approximately 17 mol % of $K_2O$, approximately 18 mol % of $K_2O$, approximately 19 mol % of $K_2O$, approximately 20 mol % of $K_2O$, approximately 21 mol % of $K_2O$, approximately 21.5 mol % of $K_2O$, approximately 22 mol % of $K_2O$, approximately 22.5 mol % of $K_2O$, approximately 23 mol % of $K_2O$, approximately 23.5 mol % of $K_2O$, approximately 24 mol % of $K_2O$, approximately 25 mol % of $K_2O$, approximately 26 mol % of $K_2O$, approximately 27 mol % of $K_2O$, approximately 28 mol % of $K_2O$, approximately 29 mol % of $K_2O$, or approximately 30 mol % of $K_2O$, among others.

With continued reference to FIG. 1, in one or more embodiments, when network-forming component 132 includes at least 80 mol % and no greater than 95 mol % of $P_2O_5$ with respect to phosphate glass matrix 104, the phosphate glass matrix 104 may have a glass melting temperature that is at least 400° C. and no greater than 600° C. For the purposes of this disclosure, a "glass melting temperature" is a required processing temperature or temperature range at/within which a mixture of precursors transforms from a nonfluidic state into a fluidic state. Once cooled down, the fluidic mixture of precursors solidifies to form glass. Glass melting temperature may be contrasted with glass transition temperature despite that the two may share overlapping numerical values for a particular material. For the purposes of this disclosure, a "glass transition temperature ($T_g$)" is a temperature at which an amorphous material, such as glass or certain polymers, transitions from a hard and brittle state to a more rubbery or viscous state. Below $T_g$, the material behaves like a solid, but as the temperature increases past $T_g$, the molecular chains gain enough mobility to exhibit more flexibility and fluidity, though the material does not fully melt. As nonlimiting examples, the glass melting temperature may be from 400° C. to 420° C., from 420° C. to 440° C., from 440° C. to 460° C., from 460° C. to 480° C., from 480° C. to 500° C., from 500° C. to 520° C., from 520° C. to 540° C., from 540° C. to 560° C., from 560° C. to 580° C., or from 580° C. to 600° C., among others. As further nonlimiting examples, the glass melting temperature may be approximately 400° C., approximately 420° C., approximately 440° C., approximately 460° C., approximately 480° C., approximately 500° C., approximately 520° C., approximately 540° C., approximately 560° C., approximately 580° C., or approximately 600° C., among others.

With continued reference to FIG. 1, in one or more embodiments, when network-forming component 132 includes at least 45 mol % and no greater than 55 mol % of $P_2O_5$ with respect to phosphate glass matrix 104, the phosphate glass matrix 104 may have a glass melting temperature that is at least 1,000° C. and no greater than 1,200° C. As nonlimiting examples, the glass melting temperature may be from 1,000° C. to 1,020° C., from 1,020° C. to 1,040° C., from 1,040° C. to 1,060° C., from 1,060° C. to 1,080° C., from 1,080° C. to 1,100° C., from 1,100° C. to 1,120° C., from 1,120° C. to 1,140° C., from 1,140° C. to 1,160° C., from 1,160° C. to 1,180° C., or from 1,180° C. to 1,200° C., among others. As further nonlimiting examples, the glass melting temperature may be approximately 1,000° C., approximately 1,020° C., approximately 1,040° C., approximately 1,060° C., approximately 1,080° C., approximately 1,100° C., approximately 1,120° C., approximately 1,140° C., approximately 1,160° C., approximately 1,180° C., or approximately 1,200° C., among others.

With continued reference to FIG. 1, in one or more embodiments, device 100 may be manufactured from a glass melt in a silica crucible. For the purposes of this disclosure, a "glass melt" is a homogeneous, fluidic mixture prepared by melting one or more chemicals and capable of solidifying into glass upon cooling. In some cases, the glass melt may be prepared from a mixture of precursors. The mixture may include chemicals such as without limitation $(NH_4)_3PO_4$, $CaCO_3$, $Na_2HPO_4$, and/or the like. Additional details will be provided below in this disclosure.

With continued reference to FIG. 1, device 100 has a dissolution rate 140 of at least 50 mg $cm^{-2}$ $hr^{-1}$. As nonlimiting examples, dissolution rate of device 100 may be from 50 mg $cm^{-2}$ $hr^{-1}$ to 100 mg $cm^{-2}$ $hr^{-1}$, from 100 mg $cm^{-2}$ $hr^{-1}$ to 200 mg $cm^{-2}$ $hr^{-1}$, from 200 mg $cm^{-2}$ $hr^{-1}$ to 500 mg $cm^{-2}$ $hr^{-1}$, from 500 mg $cm^{-2}$ $hr^{-1}$ to 1,000 mg $cm^{-2}$ $hr^{-1}$, from 1,000 mg $cm^{-2}$ $hr^{-1}$ to 1,500 mg $cm^{-2}$ $hr^{-1}$, from 1,500 mg $cm^{-2}$ $hr^{-1}$ to 2,000 mg $cm^{-2}$ $hr^{-1}$, from 2,000 mg $cm^{-2}$ $hr^{-1}$ to 2,500 mg $cm^{-2}$ $hr^{-1}$, from 2,500 mg $cm^{-2}$ $hr^{-1}$ to 3,000 mg $cm^{-2}$ $hr^{-1}$, from 3,000 mg $cm^{-2}$ $hr^{-1}$ to 3,500 mg $cm^{-2}$ $hr^{-1}$, or from 3,500 mg $cm^{-2}$ $hr^{-1}$ to 3,700 mg $cm^{-2}$ $hr^{-1}$, among others. As further nonlimiting examples, dissolution rate of device 100 may be approximately 50 mg $cm^{-2}$ $hr^{-1}$, approximately 100 mg $cm^{-2}$ $hr^{-1}$, approximately 200 mg $cm^{-2}$ $hr^{-1}$, approximately 500 mg $cm^{-2}$ $hr^{-1}$, approximately 1,000 mg $cm^{-2}$ $hr^{-1}$, approximately 1,500 mg $cm^{-2}$ $hr^{-1}$, approximately 2,000 mg $cm^{-2}$ $hr^{-1}$, approximately 2,500 mg $cm^{-2}$ $hr^{-1}$, approximately 3,000 mg $cm^{-2}$ $hr^{-1}$, approximately 3,500 mg $cm^{-2}$ $hr^{-1}$, or approximately 3,700 mg $cm^{-2}$ $hr^{-1}$, among others. For the purposes of this disclosure, a "dissolution rate" is the rate at which a substance dissolves or breaks down, for instance upon contact with a solvent medium. A dissolution rate may be expressed using any unit deemed suitable by a person of ordinary skill in the art, upon reviewing the entirety of this disclosure. As a nonlimiting example, a dissolution rate may be expressed as the mass of matter (e.g., in milligram or mg) dissolved per unit time (e.g., per hour) per unit cross-sectional area (e.g., per $cm^2$), consistent with details described above.

With continued reference to FIG. 1, in order to ensure that device 100 does not remain inside a patient's body for an extended period of time, it is generally advantageous to increase the dissolution rate of device 100, with a few exceptions as described in further detail below. In some cases, device 100 may be configured to have a tunable dissolution rate 140, depending on the exact use case to which the device 100 is applied. As a nonlimiting example, a first surgical procedure may require a longer period of support by device 100, such as without limitation due to wider incision. Accordingly, device 100 may be configured to have a relatively slower dissolution rate 140. As another nonlimiting example, a second surgical procedure may not require device 100 to be in place upon the completion of the procedure. Accordingly, device 100 may be configured to have a relatively faster dissolution rate 140 in order to prevent long-term issues, such as without limitation stenosis. Dissolution rate 140 of device 100 may be fine-tuned by changing the chemical composition of phosphate glass matrix 104, such as without limitation by changing the ratio between network-forming component 132 and modifier 136. As a nonlimiting example, as the molar ratio between network-forming component 132 and modifier 136 increases, dissolution rate 140 may decrease accordingly, and vice versa.

With continued reference to FIG. 1, in one or more embodiments, device 100 may be configured to dissolve into physiological ions with negligible cytotoxic effects instead of fragmenting into pieces of foreign materials. For the purposes of this disclosure, a "physiological ion" is an ionic species that is naturally present in the bodily fluid of a patient and/or participating in one or more physiological processes therein. As nonlimiting examples, device 100 may dissolve into physiological ions such as without limitation $Na^+$, $K^+$, $Ca^{2+}$, $PO_4^{3-}$, $HPO_4^{2-}$, $H_2PO_4^-$, and/or the like. For the purposes of this disclosure, a "cytotoxic effect" is the capacity of a substance, treatment, or material to damage or kill cells. Accordingly, in order to evaluate and/or prevent potential cytotoxic effects, cytotoxicity testing is commonly performed to ensure that a drug or medical device does not induce any harmful impact on surrounding healthy tissues or cells when used in treatments. As a nonlimiting example, a material associated with or characterized by one or more cytotoxic effects may release harmful by-products or cause inflammation, making it unsuitable for implantation or contact with human tissue. Cytotoxic effects are particularly relevant in the evaluation of drugs, medical implants, and devices, where the impact on living cells must be carefully assessed. For medical devices, such as without limitation the invention described herein, cytotoxic effects may be of critical consideration in biocompatibility assessments, as excessive cell damage may lead to poor healing, device rejection, and/or systemic toxicity, among others. Additionally, foreign materials, including without limitation shards or similar structures with sharp edges or vertices, may pose safety hazards to a patient. As a nonlimiting example, a shard that remains in a blood stream may pierce through a blood vessel or an organ and cause bleeding. In order not to fragment into pieces of foreign materials, device 100 may be configured to have a steady, uniform dissolution rate across different locations, such as without limitation difference edges, vertices, facets, surfaces, and/or the like. In some cases, in order not to fragment into pieces of foreign materials, tubular shape 108 may have a bulging middle region and tapered ends. In some cases, in order not to fragment into pieces of foreign materials, tubular shape 108 may have a thickness 120 at its center that is larger than the thickness 120 at its two ends, forming a gradient in between. Additionally, and/or alternatively, in some cases, device 100 may be configured to have a dissolution rate 140 below a certain threshold, such as without limitation by fine-tuning its chemical composition, consistent with details described above. Such designs, either in singularity or in combination, may ensure that device 100 holds together as a single piece instead of breaking apart during its course of dissolution.

With continued reference to FIG. 1, in one or more embodiments, device 100 may have a dissolution time 144 that is at least 2 minutes and no greater than 30 minutes. For the purposes of this disclosure, a "dissolution time" is the time it takes for device 100 to completely dissolve. Dissolution time 144 may be used instead of, or in addition to, dissolution rate 140 to quantify how fast or slowly device 100 may dissolve upon contacting a solvent medium, such as without limitation upon a restoration of blood flow after a surgical procedure. It is also worth noting that, compared to dissolution rate 140, which is more likely an intensive property that depends on the chemical composition of device 100/phosphate glass matrix 104 only, dissolution time 144 may be an extensive property that scales with the size and/or mass of device 100. Therefore, dissolution rate 140 and dissolution time 144 may characterize device 100 from complementary perspectives. As nonlimiting examples, dissolution time 144 may be from 2 minutes to 5 minutes, from 5 minutes to 10 minutes, from 10 minutes to 15 minutes, from 15 minutes to 20 minutes, from 20 minutes to 25 minutes, or from 25 minutes to 30 minutes, among others. As further nonlimiting examples, dissolution time 144 may be approximately 2 minutes, approximately 5 minutes, approximately 10 minutes, approximately 15 minutes, approximately 20 minutes, approximately 25 minutes, or approximately 30 minutes, among others.

With continued reference to FIG. 1, in one or more embodiments, device 100 may further include a volume of storage medium 160 within which phosphate glass matrix is submerged. This design may be implemented due to the moisture-sensitive nature of phosphate glass matrix 104. In some cases, storage medium 160 may include a neat non-polar solvent such as without limitation neat ethanol, neat isopropanol, or the like. In some other cases, storage medium 160 may include a moisture-free, gas-phase storage medium such as without limitation dry air, dry nitrogen, dry argon, or the like. Storage medium 160 may be contained in container deemed suitable by a person of ordinary skill in the art, upon reviewing the entirety of this disclosure, such as without limitation a vial, an ampule, or the like. The volume of storage medium 160 may include any volume that is sufficient to submerge device 100 without creating unnecessary burden for transportation. As nonlimiting examples, the volume of storage medium 160 may be from 500 μL to 1 mL, from 1 mL to 2 mL, from 2 mL to 5 mL, from 5 mL to 10 mL, from 10 mL to 15 mL, from 15 mL to 20 mL, or the like. In some cases, storage medium 160 may be purified using a solvent system to remove the trace amount of water therein before use. In some cases, storage medium 160 may be introduced using a gas displacement apparatus, where dry nitrogen gas, dry argon, or the like is supplied as a stream to displace the air within a container that contains device 100. In some cases, device 100 may be packed under a nitrogen gas or argon atmosphere, such as without limitation inside a glovebox. In some cases, a container that contains device 100 and storage medium 160 may be sealed, such as without limitation using a septum or Teflon tape, to maintain a moisture-free environment therein.

Referring now to FIG. 2, a method 200 of manufacturing device 100 for supporting surgical procedures is illustrated. At step 205, method includes preparing a glass melt in a silica crucible. For the purposes of this this closure, a "silica crucible" is a high-temperature-resistant container comprising silicon dioxide ($SiO_2$). Silica crucibles are often used in laboratory and industrial applications for holding and heating substances to extreme temperatures. In some cases, silica crucibles may be designed to withstand temperatures exceeding 1,000° C. without significantly deforming or reacting with the materials they contain, making them ideal for processes such as without limitation melting metals, annealing, and/or sintering, among others. Silica crucibles are often valued for their thermal stability, low reactivity, and resistance to thermal shock, making them suitable for high-purity applications such as semiconductor manufacturing and the melting of glass, as described herein in this disclosure. Silica crucibles are commonly used in processes where contamination is expected to be minimal and high chemical inertness is required. This step may be implemented with reference to details described above in this disclosure and without limitation. In one or more embodiments, preparing the glass melt may include preparing the glass melt from a mixture of precursors. The mixture may include chemicals such as without limitation $(NH_4)_3PO_4$, $CaCO_3$, $Na_2HPO_4$, and/or the like, consistent with details described above. In one or more embodiments, a plurality of starting materials may be melted to produce a desired composition, which may be subsequently quenched to form a frit. The frit may then be heated to a suitable working temperature and melted, as described elsewhere in this disclosure, and tubes may accordingly be drawn therefrom.

With continued reference to FIG. 2, at step 210, method 200 further includes injecting a gas bubble into the glass melt. This step may be implemented with reference to details described above in this disclosure and without limitation. For the purposes of this disclosure, a "glass bubble" is a volume of gas or gas mixture that, once introduced, occupies a volume within a glass, e.g., phosphate glass matrix 104. In some cases, glass bubble, upon shaping, creates tubular shape 108 with a hollow center. As a nonlimiting example, the gas bubble may be injected manually by blowing a short burst of air through a blowpipe. As another nonlimiting example, the gas bubble may be introduced via mechanical means, such as without limitation using a compressed air system, an air pump, a gas cylinder, a blowing machine, or the like.

With continued reference to FIG. 2, at step 215, method 200 further includes shaping the glass melt containing the gas bubble into a phosphate glass structure having a tubular shape. This step may be implemented with reference to details described above in this disclosure and without limitation. For the purposes of this disclosure, a "phosphate glass structure" is a structure containing phosphate glass. A phosphate glass structure has the same chemical composition as phosphate glass matrix 104 described above and may be transformed into device 100 after further processing. In one or more embodiments, shaping the glass melt may include extruding the glass melt using an extruder. For the purposes of this disclosure, an "extruder" is a machine used to shape materials by forcing them through a die to create a continuous profile. In glass manufacturing, an extruder works by applying heat and pressure to glass materials, forming them into specific shapes as they are pushed through a nozzle or mold. An extruder may be used for manufacturing glass fiber, glass tubing or rods, and/or specialty glass components, among others. The manufacturing process that involves the use of an extruder is accordingly termed extrusion. To perform glass extrusion, a high temperature is required to keep the glass in a semi-molten state and ensure a smooth flow through the die without fracturing. Such an extrusion process may require precise control over temperature and pressure for successful shaping. In some cases, an extruder may be controlled using a computing device. Additional details will be provided below in this disclosure. In one or more embodiments, shaping the glass melt may further include shaping the glass melt into a tubular shape to create one or more structural features such as without limitation a smooth outer surface 148, a smooth edge 152, and/or one or more tapered ends 156, among others, consistent with details described above.

With continued reference to FIG. 2, at step 220, method 200 further includes cooling the phosphate glass structure below its glass melting temperature. This step may be implemented with reference to details described above in this disclosure and without limitation. In one or more embodiments, cooling the phosphate structure may include cooling the phosphate structure down to room temperature. In one or more embodiments, cooling the phosphate structure may include cooling the phosphate structure using an annealer. For the purposes of this disclosure, an "annealer" is a specialized oven or furnace used in glass manufacturing to slowly cool glass products after they have been shaped or formed. This process, known as annealing, relieves internal stresses that develop in the glass during rapid cooling. If these stresses are not properly relieved, the glass may crack or break easily under mechanical or thermal loads. An annealing process typically includes three stages: a heating stage, a soaking stage, and a gradual cooling stage. A person of ordinary skill in the art, upon reviewing the entirety of this disclosure, will be able to recognize how step 220 may be properly implemented.

With continued reference to FIG. 2, at step 225, method 200 further includes truncating the phosphate glass structure into a desired length to form device 100. The desired length may include any suitable length 128 of device 100 described above or otherwise recognized by a person of ordinary skill in the art, upon reviewing the entirety of this disclosure. This step may be implemented with reference to details described above in this disclosure and without limitation. In one or more embodiments, the method may further include submerging the device in a volume of storage medium, consistent with details described above.

Example 1

Tissue repair and wound closure are typically performed using mechanical methods, which are necessary to bring the wound surfaces into apposition and provide sufficient strength to avoid dehiscence. For vessel anastomosis, in particular, it is difficult to keep the lumen open during the process and additional damage to the vessel is possible when a suture needle catches the back side of the vessel. These two issues could be ameliorated by use of a temporary stent that may hold the vessels open and keep suture needles from reaching the back side of the vessel, which would in turn increase the speed of the process and reduce the incidence of adverse effects. Microvascular surgery, in particular, would benefit from having a rigid support structure in place to support the vessel during operation, especially for anastomosis procedures where a severed vessel must be rejoined. This support would ideally be short-lived, robust, non-toxic, and dissolve smoothly into non-toxic products.

Device 100 dissolves quickly, survives handling until blood-flow is restored, and dissolves into physiological ions. Surgeons that have worked with devices 100 have endorsed them for these favorable attributes and have noted that their inclusion makes surgical procedures easier. Since microvascular surgery is currently performed without a stent in place, a high level of skill is often required to complete the procedure safely. Device 100 could lower the skill required to successfully complete a microvascular operation, thus allowing for more surgeons to be comfortable completing the procedure.

Currently, there is no suitable temporary support material for tissue repair and microvascular surgery. As such, there is an inherent risk of "backending" when suturing, where the needle pokes through the entire vessel. By placing a temporary rigid support like device 100, there is a physical block that prevents backending from occurring. This mechanism decreases the risk involved with a surgical procedure.

Compared to other existing temporary stents, device 100 dissolves at a much more rapid rate, typically within tens of minutes when blood flow is restored. Other temporary stents dissolve on timescales of days to months, which has been shown to cause complications, consistent with details described above. Microvascular surgery has been demonstrated using polyvinyl alcohol (PVA) stents, though their slow dissolution caused turbulence at the surgical site and eventually led to stenosis. A rapid-dissolving stent removes long-term turbulence as a factor. Further, its byproducts are physiological ions as opposed to polymeric stents or other bioglasses with a high silica content.

The most prominent difference between the approach described herein and other arts is that microvascular surgery currently does not use a stent to support vessels during operation. There are no other approved devices that fill this void for surgeons. As previously stated, a rigid stent in place would reduce the risk of backending. There are other potential temporary materials, but those materials dissolve at much slower rates, thus increasing the risk of stenosis, and degrade into non-physiological products with potentially higher cytotoxicity.

The invention described herein is a medical device in the form of a phosphate glass stent. It is made with biocompatible glass primarily and may be used to assist microvascular surgery procedures. The dimensions of the stent may be tunable depending on the size of the vessel. Likewise, adjustments to the composition can be made to tune dissolution rate 140 over a wide range.

Device 100 is currently stored and delivered in absolute ethanol to increase its shelf life. This storage method may also help keep device 100 sterile. Device 100 may not be stable in humid environments, and thus may preferably be kept in ethanol until needed. Device 100 may last tens of minutes in the open air before any significant surface deliquescence occurs.

Device 100 may be inserted into one end of a severed vessel before joining the other end over the device 100. Then, a surgical procedure can be done to repair the vessel. After blood flow is restored, device 100 may dissolve at rate that depends on specific requirement of the procedure, though typically within 10-60 minutes.

Devices 100 are currently showing strong promise in small animal studies and are being moving toward large animal (sheep) tests. Devices 100 may be manufactured in final form/final process, ideally in a GMP/GLP environment.

Device 100 may be used as a rapidly dissolvable phosphate glass stent to provide temporary support during the use of photochemical tissue bonding (PTB) for vascular anastomosis.

PTB is an alternative light-based procedure that uses chemical reactions to achieve wound closure and has proven to be a platform technology with widespread potential application in many clinical fields, including without limitation wound closure in peripheral nerve, ophthalmology, dermatology, plastic surgery, gastrointestinal surgery, otolaryngology, and/or orthopedics, among others. Preliminary studies on bonding luminal tissue, such as blood vessel or bowel, where a circumferential, water-tight seal is essential, demonstrated the potential effectiveness of this technique, but pointed to the need for an appropriate scaffold/stent for it to be clinically viable. It is demonstrated herein that a hollow intraluminal stent is a simple and viable solution to support vascular anastomosis using PTB if the stent material is very short-lived and dissolves or degrades following re-establishment of blood flow. Building on these early trials, the feasibility of rapidly dissolvable phosphate glass based non-toxic stents has been demonstrated for use in vascular anastomosis. These results clearly demonstrate the value of PTB for reducing foreign body interactions, vessel leakage, and adhesions in such procedures and provide a strong proof-of-principle for similar procedures including, without limitation, bowel repair.

It has been demonstrated that the family of phosphate glasses described herein may provide structural support during a PTB procedure and then rapidly and safely dissolve when blood flow is restored. Phosphate glasses were selected as the target material due to their potential effectiveness and based on (i) their case of synthesis and forming into useful shapes, (ii) tunability for a wide range of dissolution rates, and (iii) dissolution into common physiological ions that are unlikely to have cytotoxic effects.

It has been demonstrated that this approach is feasible. Specifically, two families of phosphate glasses were developed to demonstrate the required rapid dissolution and the ability to be formed into tubes suitable for vascular anastomosis. These prototype stents have been inserted ex vivo into swine vessels and have been shown to be compatible with PTB dyes. Demonstration of the use of the prototype stents in the PTB process is currently ongoing.

A broad range of phosphate glass compositions were melted and evaluated to map the effects of its composition on the overall performance of a candidate glass. This survey resulted in multiple potential candidate glasses for use in PTB. Multiple, sometimes competing, requirements were tuned, balanced, and optimized for a successful stent. Two families of phosphate glasses were identified: ultraphosphates (with 80-90 mol % of $P_2O_5$, CaO, and small additions of $B_2O_3$ and $SiO_2$) and metaphosphates (with 40-50 mol % of $P_2O_5$, CaO, $Na_2O$, $K_2O$, and potentially a small amount of $TiO_2$ or $SiO_2$) that are capable of cleanly dissolving within a short period of time and being formed into tubes with a suitable geometry.

Tubes with an outer diameter from 2 millimeters to 4 millimeters were drawn using these phosphate glasses. Specifically, a small bubble was blown into remelted glass, and the bubble was then hand-drawn to form the desired tube. Tubes were then sectioned and stored in vials for transport. Early formulations were subject to rapid attack by moisture in the atmosphere and were stored and shipped in dry air or nitrogen. Later formulations were stable in the atmosphere for days to weeks at least. These candidate tubes were delivered for further evaluation in surgical procedures.

The tubes were evaluated in an ex vivo simulated PTB process, and feedback on their case-of-use and compatibility was collected accordingly. Based on such feedback, dissolution rate 140 was further slowed down from the initial target, so that the tubes were present for a longer time period, and this change also reduced the amount of acid produced at one time to keep PTB dyes from bleaching.

Photochemical Tissue Bonding

Tissue repair and wound closure have traditionally been performed using mechanical methods such as suture, staples, couplers, and clips. These devices are necessary to bring the wound surfaces into apposition and provide sufficient strength to avoid dehiscence through the early wound healing period until the tissue repair has developed sufficient strength to function independently. These methods, although effective for wound closure, are associated with a variety of downstream effects that can prove deleterious to the ultimate repair. Some are associated with foreign body response, leading to increased inflammation at the repair site that can negatively impact aspects of wound healing. Inflammatory responses can lead to excessive scarring at the repair site. Needle and staple passage can cause trauma to the tissue itself and may also act as a nidus for infection. Additionally, these approaches may be impractical for use in certain small, delicate, or friable tissues (e.g., vocal fold).

As a result, there has been great interest in alternative methods for wound closure in medical research. Glues, both chemical (e.g., cyanoacrylates) and biological (e.g., fibrin), have been investigated in many tissues and some, such as Dermabond, have been accepted for use in external tissues such as skin. However, these glues can also trigger a strong inflammatory response, making them unsuitable for some wound closure uses. Energy-based strategies, such as "laser welding", have also been investigated. Laser welding requires a high-power laser system that heats the tissue at a wound closure interface to a temperature that is sufficiently high to denature structural proteins like collagen and form an amorphous weld to hold the tissue surfaces together. Laser welding has not found clinical acceptance due to the collateral thermal damage to adjacent tissue and a tendency for excessive scarring to result. To overcome the barrier of thermal damage to tissue, an alternative light-based approach was implemented that used chemical reactions rather than heat to achieve wound closure, which is termed "Photochemical Tissue Bonding" (PTB), as described above.

PTB uses a nontoxic, photoactive dye called Rose Bengal (RB) that is applied to the wound surfaces before apposition and is activated using low power (~500 $mW/cm^2$) green light (typically at a wavelength of 532 nm (KTP laser) or 550 nm (LED)) to form reactive intermediates that initiate cross-linking reactions between collagen molecules across the wound surface. The multitude of covalent chemical bonds may act as "nanosutures" and are cumulatively responsible for a strong wound closure. The lower-power nature of the illumination avoids temperature increases of more than a few degrees, thereby avoiding denaturation and retaining the structural integrity of the tissue at the repair site with no indication of any phototoxicity to the tissue.

PTB has proven to be a platform technology with widespread potential application in many clinical fields. Preclinical studies have been successfully performed for wound closure in peripheral nerve, ophthalmology (cornea and sclera), dermatology, plastic surgery, gastrointestinal surgery, otolaryngology, and orthopedics (cartilage and tendon). A human study was also successfully performed for superficial wound closure following an excision of abnormal skin lesions. In the course of these exploratory studies, a number of critical characteristics of the process were identified. The RB solution is applied to the wound surfaces and the excess is removed after one minute. Overall, the binding strength between the wound surfaces may depend on the surface area involved in the bond and the wound surfaces may need to be brought into intimate contact for the procedure to be effective. A watertight seal may form as a result of photoactivation. Thus, means for ensuring surface-to-surface contact may be crucial for the integrity of the bond and various methods have been devised to appose tissues securely and reproducibly. An interesting subset of the general problem is a luminal tissue, such as blood vessel or bowel, where a circumferential, water-tight seal may be essential.

Need for Scaffolds in PTB

Early studies of PTB for vasculature closure were focused on two factors: (1) tissue overlap to create a strong bond and (2) ensuring the lumen remains open with good contact at the wound closure interface. A proximal-in-distal cuff was adopted with a few millimeters of overlap for the bond area, supported by a catheter during the illumination procedure. The catheter was introduced via a side branch for a proof-of-principle rodent study, which may not be a clinically relevant approach. In order to simplify the problem of intraluminal support, PVA polymer stents were introduced to support the cuff during the procedure. Patent anastomoses were achieved in the acute sense, but longer-term problems arose due to turbulence of blood flow that ultimately led to stenosis over a period of weeks. In summary, a hollow intraluminal stent is a simple and viable solution to support vascular anastomosis using PTB if the stent material is very short-lived and dissolves or degrades following re-establishment of blood flow.

In addition to the short dissolution time 144, ideally 2-30 min, once blood flow is restored, device 100 is expected to be sufficiently rigid to support the bond interface and sufficiently robust to survive handling and use without being damaged. Both device 100 itself and its dissolution products are expected to be nontoxic. Device 100 is expected to dissolve smoothly rather than fragment into chunks of foreign material in the blood stream. Device 100 is expected to have a smooth outer surface and ideally tapered ends to case insertion and minimize damage to the vessel being repaired. Device 100 may be expected to be processable into small tubes with lengths from 5 millimeters and 20 millimeters. Outer diameters 112 of device 100 may be from 1 millimeter to 5 millimeters. The outer diameter-to thickness ratio may be approximately 5. Device 100 may be easily packaged and sterilized and has demonstrated a long shelf life.

Based on such an assessment, a family of phosphate glasses with tunable dissolution rate and their methods of manufacture were developed, and the use of these phosphate glasses in a simulated environment were demonstrated. Additionally, due to the high solubility in aqueous media required for this application, initial packaging and storage solutions were developed to protect the stents and scaffolds from atmospheric humidity before use.

Glass Selection and Formation

Glass composition may be key to developing a phosphate glass stent that rapidly dissolves in a physiological environment. A set of glasses encompassing a range of network forming ($P_2O_5$) and modifier metal oxides were developed. $P_2O_5$ is highly reactive. Therefore, in general, the greater the percentage of $P_2O_5$ present in the composition, the faster dissolution rate 140 will be. The initial target composition for phosphate glasses included at least 65 mol % $P_2O_5$. Additionally, specific amounts of modifying metal oxides were included to further tailor dissolution rate 140. These modifier oxides included $Na_2O$, $K_2O$, and CaO. The addition of CaO helps to stabilize the glass, slowing the dissolution, while the addition $Na_2O$ and $K_2O$ help to limit the tendency to crystallization, making the glass more easily processible.

The additions of $B_2O_3$, $SiO_2$, and $TiO_2$ may further stabilize the phosphate glass and improve its processability.

Metal oxide compositions of ≤5% CaO and ≤35% $(Na/K)_2O$ were chosen for initial formulation. These initial compositions were further tuned based on their experimental dissolution rates to achieve target dissolution rates 140. As a nonlimiting example, the target dissolution rates may be from 50 mg $cm^{-2}$ $hr^{-1}$ to 3700 mg $cm^{-2}$ $hr^{-1}$, based on the expected stent sizes, glass densities, and the desired dissolution times 144. Once a set of candidate glass compositions were selected for phosphate glass stents, glass preforms were then created for stent fabrication.

A melt-quench method of glass fabrication was used to create a range of glass formulations and the glass preforms, from which prototype glass stents were drawn. Glass components (e.g., $(NH_4)_3PO_4$, $CaCO_3$, $Na_2HPO_4$) were combined together in a crucible. The choice of crucible may be critical for the outcome of the manufacturing process. Typically, a Pt crucible would be used for its high temperature capability and general inertness, but phosphate glasses may damage Pt crucibles. Therefore, inexpensive silica crucibles were used instead. Silica crucibles have sufficient temperature capability but may contribute about 1% $SiO_2$ to the glass composition. This small fraction of $SiO_2$ was accounted for in the compositional design and did not significantly impact performance of the phosphate glass. Glass components were fused using a furnace to create a glass melt, and the powder mixture was heated to a temperature from 500° C. to 1,200° C. for one to three hours in ambient atmosphere to ensure the components have been thoroughly combined into a glass melt. The glass melt was then poured into a preheated mold where it was annealed and then slowly cooled to create a preform that can be used to draw glass stents.

Glass Forming

The two main ways that glass rods or tubes can be made are by extrusion and drawing. In extrusion, hot or cold material is pressed through a die to give the material its final shape, generally with good surface finish and well-controlled dimensions. The process, however, may be relatively equipment intensive, requiring a different die for each geometry desired and machinery for applying moderately high pressures. In contrast, a drawing process involves pulling material from a heated preform at a controlled speed to stretch and thin the material. This method may create additional flexibility, allow a user to modify a variety of variables more easily, and produce samples of different sizes faster than extrusion. Due to its case in changing variables, fiber drawing may be used as the method to produce glass stents. It is worth noting that the precise control and reproducibility provided by extrusion may also make it a suitable manufacturing method. Additional details will be provided below in this disclosure.

The major factors that determine the final diameter and wall thickness of the glass stents may include the viscosity and the pulling speed of the preform. Before experimenting with the pulling speed, a temperature-viscosity relationship of the glass was established and evaluated to determine an appropriate working temperature range and achieve an appropriate glass viscosity ($10^6$-$10^7$ Pa·s) with less trial and error.

To make the phosphate glass stents, preforms were heated to their working temperature and then drawn out at a range of speeds. The geometry of the resulting stents was measured. Iteration on the dimensions of the starting preforms and the drawing rate helped identify a set of conditions to generate stents with outer diameters 112 from 1 millimeter to 5 millimeters and an outer diameter-to-thickness ratio of approximately 5.

Characterization and Testing

The glasses made at each step were characterized. Thermal properties, such as without limitation glass transition temperature ($T_g$), were measured by differential scanning calorimetry (DSC), and optical microscopy was used to measure the geometry and observe the dissolution of the formed glass stents.

Initial dissolution rates were measured by immersing a phosphate glass bead with a defined geometry and mass in a phosphate buffered saline (PBS) solution and images were acquired at intervals. The pH of the PBS solution was monitored to ensure that the dissolution of the glasses is not causing the solution to become either too acidic or too basic.

Once prototype stents with the desired properties were prepared, they were evaluated in a simulated PTB anastomosis procedure using arteries and veins harvested from previously euthanized animals, such as without limitation swine. After the PTB process, the vessels containing the stents were connected to a simulated circulation system and the dissolution of the stent were monitored. The quality of the anastomosis was assessed by a combination of burst pressure and tensile testing.

Technical Results

Two families of candidate glasses that met target properties were identified. These glasses were hand blown into prototype stents for evaluation by surgeons. Through the surgeons' feedback and quality control testing, the candidate formulations were refined, and prototype stents were made to produce fast-dissolving, stable phosphate glass stents for use in PTB anastomosis.

Glass Selection and Formation

Each glass melt was prepared by following a relatively standard procedure with some tuning of melting times and temperatures. The batch components (i.e., precursors) were first crushed in a mortar and pestle to create a more homogenous starting mixture. A crucible was then filled to ~50% with the batch components to prevent any spillage from foaming during off-gassing. The crucible was then placed in a furnace for 1-2 hours while being swirled halfway through the melting process to facilitate mixing. The molten glass was either pulled into tubes directly from the crucible or cast into a heated mold for later analysis.

Ultraphosphate Glasses

The first regime investigated was the ultraphosphate region, where the $P_2O_5$ content is greater than 50 mol % with respect to phosphate glass matrix 104. While quaternary blends (i.e., blends containing $P_2O_5$, $K_2O$, $Na_2O$, and CaO) were initially investigated, focus was later shifted to binary blends to gain a better understanding of how each modifier affects the final glass product. These binary blends included 90 mol % $P_2O_5$ and 10 mol % of either CaO, $K_2O$, or $Na_2O$. Each modifier served to variably increase the stability and decrease the dissolution rate of the phosphate glass. The modifiers ranked as CaO>>$Na_2O$>$K_2O$ in terms of increasing stability and decreasing dissolution rate 140 (i.e., CaO has the highest stability and the lowest dissolution rate 140). This test also gave way to the first candidate formulation of 90 mol % $P_2O_5$ and 10 mol % CaO. It also revealed the importance of including calcium as a stabilizing agent. Blends without calcium were often too unstable, and future candidate glasses all included some amount of calcium.

Generally, ultraphosphate glasses were found to have higher dissolution rates 140 with a lower stability. Higher field strength modifiers may be necessary to control both the dissolution and affinity for atmospheric water. While a quick dissolution may be desired for the stents, the high phosphate content may result in a highly acidic environment around the dissolving stent. The initial candidate glass showed this problem, so modifiers with a higher field strength than calcium were added to further slow the dissolution rate to control the release of acid from these stents. These modifiers included $B_2O_3$ and $SiO_2$ for a glass composition of 84 mol % $P_2O_5$, 3 mol % $B_2O_3$, 3 mol % $SiO_2$, and 10 mol % CaO. For the purposes of this disclosure, "field strength" is a parameter describing the extent of ionic character within an ionic compound. As a nonlimiting example, field strength may be used to describe ionic bonds between metal cations and oxide anions; bonds involving components with a low field strength may possess a higher amount of ionic character, whereas bonds involving components with a high field strength may possess a higher degree of covalency and/or directionality with respect to their bonding environment (i.e., may be more covalent in nature).

Ultraphosphate glasses were shown to have an inherent advantage in processing, as they were able to be melted at much lower temperatures, typically 500° C. The lower melting temperature allows more water content to be present in the glass network, which increases dissolution rate 140 even further. The glass transition temperatures ($T_g$) were also found to be much lower than other blends, which allows for more working time to produce stents from the molten glass.

Metaphosphate Glasses

The second regime investigated was the metaphosphate region of phosphate glasses, where the $P_2O_5$ content is approximately 50 mol %. The $PO_4$ units in a metaphosphate glass network would theoretically form an infinitely long polymeric chain that is beneficial to the dissolution mechanism. Potential candidate formulations in this regime included 50 mol % of $P_2O_5$ and from 5 mol % to 10 mol % of CaO, with the remainder being filled with $K_2O$, $Na_2O$, or a mixture thereof. Due to a higher content of modifier, these glasses were found to be much more stable than the ultraphosphate glasses. However, they require higher glass melting temperatures (from approximately 1,000° C. to approximately 1,200° C.) and have somewhat lower dissolution rates 140.

Processing metaphosphate glasses requires more attention to processing conditions to ensure the quality of the final glass product. In some cases, metaphosphate glass melted at lower temperatures (~1,000° C.) was found to contain trace amounts of residual carbonate from the starting materials. Therefore, the melting temperature was boosted to ~1,200° C. for candidate blends, which was found to eliminate the remaining carbonate. This change also had the effect of increasing dissolution rate 140.

Metaphosphate glasses were much more resilient to atmospheric water than ultraphosphate glasses. Most metaphosphate glasses were stored in non-humidity-controlled containers and would typically only show evidence of atmospheric attack after weeks of storage. Long-term storage may still require humidity control; however, this increased atmospheric stability is a significant improvement compared to ultraphosphate glasses given the short amount of handling time needed by surgeons.

A candidate blend was identified with a composition of 50 mol % $P_2O_5$, 22.5 mol % $K_2O$, 22.5 mol % $Na_2O$, and 5 mol % CaO. The increase in overall modifier content allowed the calcium content to drop while still producing a stable glass. CaO has a significantly lower dissolution rate 140 compared to $Na_2O$ and $K_2O$. Therefore, the decrease in calcium content counterbalanced the increase in overall modifier content and allowed metaphosphate candidates to remain within the target range of dissolution rate 140. To further stabilize this candidate formulation, 2 mol % of $TiO_2$ was added in another blend. The final candidate glasses were formed into tubes and delivered for testing. See Table 1 below for additional information.

TABLE 1

Delivered Candidate Glass Formulations with Processing Conditions, Dissolution Times in Static Phosphate Buffered Saline (PBS), and Other Relevant Notes.

| Glass Composition (mol %) | Processing | Dissolution Time | Other Notes |
|---|---|---|---|
| 90% $P_2O_5$-10% CaO | 500° C., 1 hr | ~4 minutes | Fastest dissolution, rapid atmospheric attack, significant local acid production |
| 84% $P_2O_5$, 10% CaO, 4% $B_2O_3$, 4% $SiO_2$ | 500° C., 1 hr | ~5 minutes | Fast dissolution, improved atmosphere resilience, reduced acid production |
| 50% $P_2O_5$-22.5% $K_2O$-22.5% $Na_2O$-5% CaO | 1000° C., 2 hr | ~7 minutes | Fast dissolution, good atmosphere resilience, low acid production, short working/forming time |
| 48% $P_2O_5$-22.5% $K_2O$-22.5% $Na_2O$-5% CaO-2% $TiO_2$ | 1000° C., 2 hr | ~2-3 hours | Longer dissolution, excellent atmosphere resilience, easier forming |

Glass Tube Forming

Glass tube formation was performed by hand, i.e., by blowing molten glass after a glass melt is prepared. The molten glass would first be gathered on a rod and then blown to create a pocket of air. Once the air pocket was formed, the glass was pulled with tweezers to create tubes. The workability of candidate glasses may also be crucial in deciding which formulations were viable for stents. A glass formulation with less workable time may lead to a lesser yield or potentially no yield at all. Surgeons may also require a smooth surface to place the stents in the vessel, so glass candidates with even minor crystallization problems may not be viable due to the jagged edges they may contain.

Minor changes to the formulation may drastically change the workability of a given glass formulation. The two candidate metaphosphate glasses may have drastically different workabilities upon an addition of 2 mol % $TiO_2$. Specifically, the metaphosphate blend with no $TiO_2$ would form jagged edges once pulled from the glass melt. Some tubes were made successfully, however at a much lower yield. Ultraphosphate glasses were preferred for tube formation due to their longer working time, as their lower glass melting temperature allowed ample time and care to be placed when blowing the glass tubes.

Feedback from testing indicates that the tubes meet the requirements in terms of smoothness. Some delivered tubes had outer diameters that were slightly too large, however surgeons noted that the viable tubes delivered were easily inserted into the vessel for anastomosis.

Characterization and Testing

Characterization of the phosphate glasses was required to determine the stability, dissolution rate 140, and general composition of the final formed glasses. Evaluation of prototype tubes was performed using ex vivo simulated PTB anastomosis.

Stability

All glasses produced were mechanically stable, so stability was measured in terms of how the glass reacted to atmospheric water. Many ultraphosphate glasses were readily dissolved when exposed to the atmosphere, initially becoming tacky/sticky and eventually dissolving into a thick liquid. This tendency was alleviated by storing the final tubes in containers with desiccant or backfilled with dry nitrogen gas. While ultraphosphate glasses were more prone to atmospheric dissolution, most other phosphate glasses shared the same issue at varying rates. Thus, it was determined that long-term storage would require some form of humidity control.

Dissolution Rates

Dissolution rates were determined in static phosphate buffered saline (PBS). PBS mimics the ions present in the human body, making it an easily available basis for dissolution studies. Either a tube or a molded piece of glass first had its dimensions measured and was then weighed. Then, the glass was placed in a watch glass of PBS under a microscope camera to be observed during dissolution. Time-lapse series were made for dissolution of each glass, with pictures taken every minute. Stills from one of these time-lapse sequences are included in FIG. 3, embodiment 300, which shows a complete dissolution of device 100 in static PBS over eight minutes.

During each dissolution experiment, the quality of the dissolution process was observed, particularly by looking for any fragmentation or particulate release. If the dissolution was smooth and quick, the pH of the solution was tested to determine whether the PBS buffer had been broken. Due to PBS mimicking biological ionic concentrations, if a glass does not break a static test buffer, it is likely that it would not break the flowing buffer in vivo where buffering species are dynamically replenished.

Structural Analysis

Figure 4:
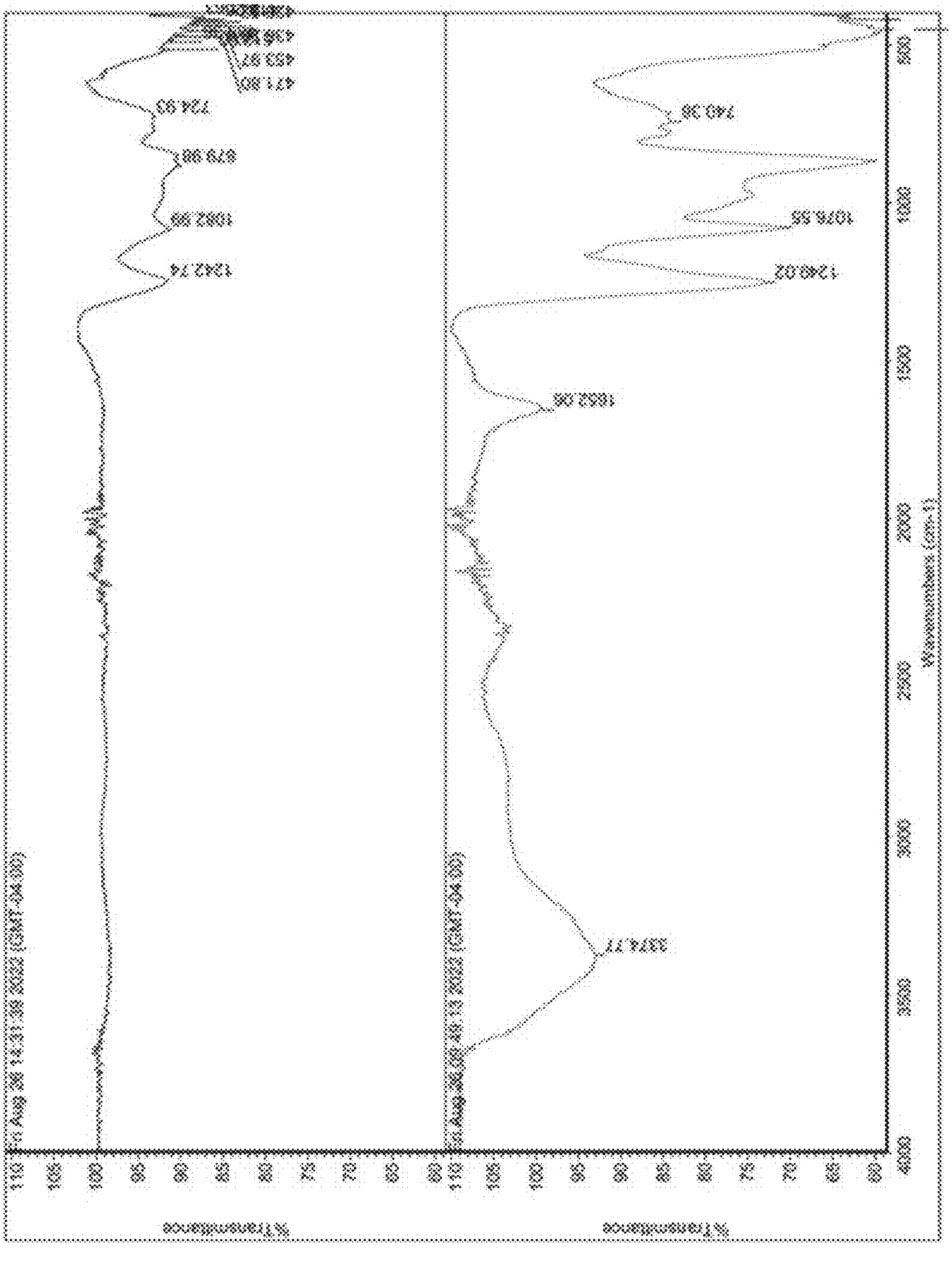
FIG. 4 includes exemplary FT-IR spectra collected from phosphate glass containing 50 mol % of $P_2O_5$, 22.5 mol % of $K_2O$, 22.5 mol % of $Na_2O$, and 5 mol % of CaO under different processing conditions; the spectrum from the top panel was collected from a sample of phosphate glass manufactured by melting precursors at 1,200° C. for three hours, whereas the spectrum from bottom panel was collected from a sample of phosphate glass manufactured by melting precursors at 1,050° C. for one hour.

FT-IR analysis was performed on select glasses to monitor the extent of reaction during glass formation and to assess the presence of water. Particularly, glasses that produced particulates upon dissolution were found to contain unreacted carbonate groups leftover from the melt-quench process. FIG. 4, embodiments 400, contains two exemplary FT-IR spectra measured using phosphate glass samples with the same composition (50 mol % of $P_2O_5$, 22.5 mol % of $K_2O$, 22.5 mol % of $Na_2O$, and 5 mol % of CaO); one sample was prepared by melting precursors at 1,050° C. for one hour (see top panel), and one sample was prepared by melting precursors at 1,200° C. for 3 hours (see bottom panel). Upon treatment under a higher temperature for a longer period of time, the peak at ~1650 $cm^{-1}$ (indicative of carbonate) completely disappeared, and the broad feature at 3370 $cm^{-1}$ (indicative of water and other unreacted hydroxyl groups) was also eliminated. Together, these observations suggest a higher temperature and a longer processing time may be necessary to fully form the glass network.

Simulated PTB Vascular Anastomosis

Figure 5:
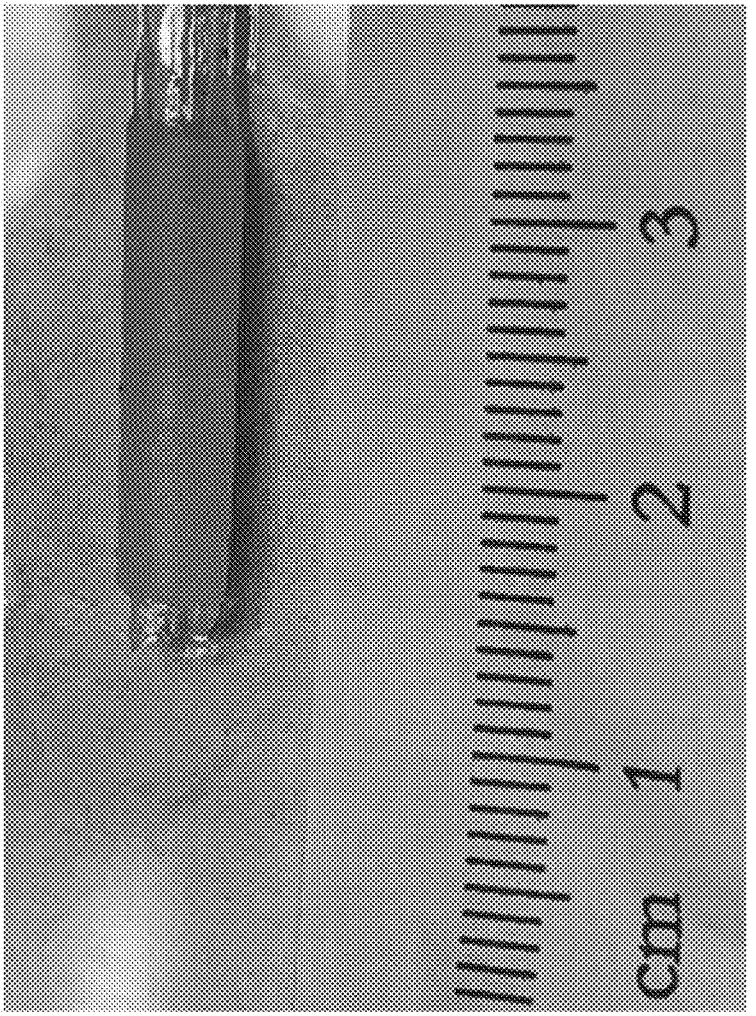
FIG. 5 includes an exemplary glass stent including 90 mol % of $P_2O_5$ and 10 mol % of CaO inserted into a swine vessel for ex vivo PTB vascular anastomosis testing.

Formulations that passed the tests described above were considered candidate glasses. These formulations were processed into tubes and sent for ex vivo testing of PTB vascular anastomosis. FIG. 5, embodiment 500, shows an exemplary device 100 inserted into a swine vessel. Feedback from the surgeons was collected to improve candidate glass formulations and manufacture of tubes.

The first batch of tubes delivered included 90 mol % of $P_2O_5$ and 10 mol % of CaO. These tubes met the goals in terms of dissolution rate 140 and geometry. Feedback from the surgeons, however, revealed that dissolution rate 140 was too fast for such composition, which caused the tubes to begin softening before the PTB anastomosis procedure was complete. The dissolution of the tube also resulted in a sharp drop in pH that bleached the RB dye, which rendered the tube ineffective for PTB procedures.

Hence, modified ultraphosphate and metaphosphate glasses were designed to have an increased stability and slower dissolution rate 140 to better showcase the technical feasibility of the approach described herein. These tubes all had an outer diameter from 3.3 millimeters to 3.8 millimeters, showed an improved stability against handling, and did not bleach the RB dye. The slightly larger outer diameter 112 made these tubes slightly too large for an anastomosis demonstration with the swine femoral artery and internal jugular veins available at the time. However, thinner tubes may be manufactured by either heating and re-drawing existing tubes from the current batch or by manufacturing new tubes.

Estimation of Technical Feasibility

In summary, two classes of candidate phosphate glasses were developed, one an ultraphosphate glass and one a metaphosphate glass. These candidate phosphate glasses have desirable dissolution times 144 and characteristics and can be formed into tubes with an outer diameter 112 between 1 millimeter and 5 millimeters. These refined prototype tubes remained stable when stored in sealed containers under normal atmosphere for more than a week and could be cut to size and handled by surgeons during a surgical procedure. Further, the refined tubes were compatible with the RB dye used in the PTB process.

Example 2

Building on the demonstration of feasibility described above in EXAMPLE 1, a continued development of phosphate glass tubes as dissolvable stents for use in PTB is described below.

Technical Approach

These prototype stents may be evaluated ex vivo, initially, then in vivo using small animals, and, finally, in larger animals to demonstrate their safety and efficacy. In parallel, suitable packaging and sterilization methods may be developed. Finally, a complete regulatory strategy to obtain FDA approval for the dissolvable stents may be developed.

Refined Glass Composition

In EXAMPLE 1, two classes of glass candidates were identified for the dissolvable stents. The first glass candidate is an alkali-poor ultraphosphate glass stabilized with $TiO_2$ or $SiO_2$, and the second glass candidate is a metaphosphate glass with mixed Na, K and Ca contents. Starting from these two classes, the compositions are further refined to achieve a combination of target performance parameters including without limitation dissolution rate 140, acidity, and workability including without limitation $T_g$ and temperature/viscosity curve, among others. At this stage, small adjustments may be made to the compositions described above to map out the local composition space in terms of performance and workability parameters. This process may help optimize the glasses and fine-tune their properties. For example, narrower stents may have a smaller mass than wider tubes, so it may be advantageous to use a slightly slower dissolving glass for narrower stents and a slightly faster dissolving glass for wider stents, such that they both dissolve completely within approximately the same amount of time.

Glass Characterization and Testing

The basic characterization includes measuring dissolution rates 140 and pH change. In addition, thermal properties of the glasses may be carefully measured through differential scanning calorimetry (DSC) and/or thermal microscopy. Finally, other basic properties of the glasses that are sensitive to structural and compositional changes may be measured, such as without limitation density, refractive index, and/or the like.

For dissolution rate 140, continuing the results from EXAMPLE 1, dissolution rate 140 may be more systematically measured using simulated body fluid at body temperature in a dynamic environment, e.g., by mixing on a shaker table or in a flow system. Dissolution of stents may be monitored optically, and the pH may be monitored using a pH meter.

Temperature/viscosity measurements may be crucial for understanding the glass stability range (working range between glass transition temperature, $T_g$, and the onset temperature of crystallization, $T_x$) and forming behavior of a glass melt, which may be crucial for successful extrusion.

Additional Characterization

Additional experiments are performed to better understand the system for reproducible and targeted modification. These experiments may include without limitation:

- Water content (TGA, DSC/MS, FT-IR spectroscopy, Raman spectroscopy, potentially $^1$H-NMR spectroscopy, etc.).
- Nitride content (SEM-EDS, FT-IR spectroscopy, Raman spectroscopy, etc.),
- Glass structure and network connectivity (FT-IR spectroscopy, Raman spectroscopy, chromatography for P-chain lengths, and $^{31}$P-NMR or XPS for information on bonding),
- Quantitative analysis of the glass composition and leached species by ICP-OES,
- In-situ measurements under humid and dry air, as well as compositional series to understand how changes in structure translate to different properties and dissolution rates 140.

Preliminary results indicate that dissolution rates 140 correlate with glass melting temperatures, indicating that different melting temperatures may impact the glass network significantly. This may occur due to a higher water content for glasses melted/processed at a low temperature (i.e., low-temperature glasses). Water acting as a modifier oxide may reduce the connectivity and stability of the glasses and significantly impact the viscosity. Mapping the glass-forming range of these pseudo-ternary system glasses ($P_2O_5$-$M_2O$/MO—$H_2O$) may provide fundamental new insights into glass chemistry of water-rich glasses, which so far have only been studied rarely, and may also be helpful for glassy materials produced via a cold, solution route, such as without limitation coacervates and/or sol-gel processed glasses, among others.

Other effects may also contribute to different behaviors of glasses melted at a higher temperature. The re-boil effect may occur in phosphate glasses, arising from a sudden release of nitrogen gas upon cooling of a phosphate melt, which at high temperatures is chemically incorporated as nitride. Alkali phosphate glasses readily form nitride glasses and have been characterized by XPS, NMR, and SEM-EDX. Nitrification may decrease dissolution rates 140.

Melting in silica crucibles might dissolve silica into a phosphate melt and stabilize the glass, as simulated in EXAMPLE 1 by adding $SiO_2$ or $TiO_2$ to the batch. Actual quantification of the $SiO_2$ by XRF, SEM, or ICP may provide important insight into the role of these high-field strength cations on the structure and properties of these glasses.

Preliminary studies of ultraphosphate melts by DSC/TGA/MS showed that up to 70 wt % of the batch material was lost during the solid-state synthesis, which is more than the expected loss due to $CO_2$, $NH_3$, and $H_2O$ in the raw materials. These studies indicate that certain volatile phosphorus-rich chemical species may have been lost as well.

Some glasses showed opacity, especially when melted at intermediate temperatures, and it is unclear how the scattering centers might be formed. Speculation ranges from crystals to bubbles to amorphous phase separation. Electron microscopy and/or X-ray diffraction (XRD) may be used to characterize these scattering centers and to avoid their formation during glass melting or forming.

Increasing the understanding of these factors may help quickly tune compositions to obtain desired properties in phosphate glasses and to reduce batch-to-batch variance.

Development of Manufacturable Tube-Forming Process

Preliminary glass tubes were successfully prepared in EXAMPLE 1 using a manual tube blowing/drawing process. While the viscosity-temperature behavior of these phosphate glasses was significantly different from common silicate glasses, nevertheless, this process was able to be adapted to produce tubes. It may be beneficial to move from this artisanal manual process to a more reproducible manufacturing process. Toward that end, an extrusion process may be developed to focus on factors such as without limitation:

- Optimization of forming/processing processes for longer tubes (that can then be cut into many smaller tapered tubes) by utilizing larger melts.
- Production of controllable and consistent tube diameters and wall thicknesses.

For an extrusion process, an induction-heater-based extrusion system may be developed, wherein the extrusion system contains a high-temperature metal vessel and a ram with a glassy graphite crucible (see FIG. 6, embodiment 600). Glassy graphite crucibles are characterized by a strong de-wetting behavior toward glasses and can be employed in an induction furnace. Temperature may be monitored and controlled via a thermocouple placed at the die, and the force applied may be monitored and controlled via a load cell between the ram and driving motor. Pre-melted glass billets may be reheated for extrusion. The size of the resulting glass tube may be controlled by the geometry of the die and the draw rate relative to the drive rate of the extrusion process.

Evaluation of Prototype Stents in PTB Anastomosis

As stated in EXAMPLE 1, refined prototype stents may be evaluated in a simulated PTB anastomosis procedure using swine or similar arteries and/or veins harvested from previously euthanized animals. After the PTB process, the vessel containing the stents may be connected to a simulated circulation system to monitor dissolution rate 140 of the stent. The quality of the anastomosis may be assessed by a combination of burst pressure and tensile testing.

Development of Sterilization and Packaging Methods

Given the very high dissolution rates 140 being targeted for this application, packaging and storage of the stents may be a significant challenge, as attack by atmospheric humidity may compromise the stents over time. In the fabrication process, the precursors, glasses, and prototype stents may be handled under inert atmosphere or at elevated temperatures, to protect them from humidity. Once manufactured, however, the prototype stents may need to be protected for storage, shipping, and handling before use. The original glass stents were stored in ethanol, which may be a good initial solution as it will also be antiseptic. Heat-scaling in metallized mylar pouches, potentially with a desiccant pouch, followed by gamma ray sterilization may also be an option. Gamma ray sterilization is a proven technique for these materials, and ethylene oxide (EtO) sterilization is also expected to be effective.

Demonstration of Prototype Stents In Vivo

Two initial studies may be performed in rats using two different stent compositions from ex vivo studies. Stent dissolution time 144 is determined as a balance between practical handling (i.e., the stent should not dissolve during the procedure) and long-term problems due to a turbulent blood flow. Thus, faster (Stent A, dissolution time 144<1 h) and slower (Stent B, dissolution time 144>2 h) dissolving formulations may be tested in rodent models to determine optimal stent for subsequent large animal testing. A long-term presence of a permanent polymer stent may cause downstream thrombosis in an anastomotic model, consistent with details described above. In addition to stent composition, it may be important to separate the contribution from photoscaling and the contribution by the presence of a stent in the vascular system. Thus, in addition to photoscaling over the stent, controls may also be required where anastomosis is performed by suturing over the stent.

The first study may be arterial anastomosis where fifty rats may undergo femoral artery transection as previously described. In the second study, a vein graft, the model including a venous interposition graft (reversed superficial epigastric vein) in the femoral artery of Sprague-Dawley rats, may be used. A total of 50 animals may undergo this procedure.

After any necessary refinement to the stents, the prototypes may be evaluated using a sheep model. Four to eight-month-old Polypay sheep (n=5; 40-45 kg) may be subject to interpositional vein graft. On postoperative day 28, the animals may return to the operating room and undergo general anesthesia for angiogram evaluation and excision of the vascular graft before euthanasia. Longitudinal and transverse segments of excised anastomoses may be removed for histological examination by an unaffiliated board-certified pathologist. Endothelial integrity, anastomotic seal, and intimal and medial thickness may be evaluated.

Regulatory Strategy

The regulatory strategy pertaining to this invention is to seek approval for dissolvable glass stents for use in vascular anastomoses, with or without the use of PTB for accomplishing the anastomosis. Based on an initial evaluation, it is anticipated that these dissolvable glass stents may be classified as Class III and require a pre-market approval (PMA) application, as it is a novel implant technology. Separately, the PTB process may also require regulatory approval, as it may likely be classified as a drug and require a New Drug Application (NDA). These two aspects may be approved separately and cross-labelled as a kit, with separate inserts; or they may be approved together as a combination product. As a combination product, the primary mode of action may likely be considered the PTB process and therefore be evaluated as a drug-led combination through the Center for Drug Evaluation and Research (CDER). As the stents alone have potential value in non-PTB anastomoses, the current plan is to obtain separate approvals for each aspect.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A self-dissolving device for microvascular anastomosis, the device comprising:
- a phosphate glass matrix having a tubular shape, the phosphate glass matrix comprising:
  - a network-forming component; and
  - a modifier, wherein the modifier comprises at most 15 mol % of CaO and does not include MgO with respect to the phosphate glass matrix, wherein:
    - the phosphate glass matrix has a glass melting temperature that is at least 1,000° C. and no greater than 1,200° C.; and
    - the device has a dissolution time ranging from 2 minutes to 30 minutes.

2. The device of claim 1, wherein the tubular shape has an outer diameter.

3. The device of claim 1, wherein the tubular shape has an outer diameter-to-thickness ratio of 4.5-5.5 and a dissolution rate of the device is selected as a function of the outer diameter-to-thickness ratio based on the dissolution time.

4. The device of claim 1, wherein the tubular shape has a length that is at least 5 millimeters and no greater than 20 millimeters.

5. The device of claim 1, wherein the device is configured to dissolve into physiological ions with negligible cytotoxic effects.

6. The device of claim 1, wherein:

the network-forming component comprises a mol % of $P_2O_5$ with respect to the phosphate glass matrix within an inclusive range consisting of one or more of from 82 mol % to 84 mol % of P2O5, from 84 mol % to 86 mol % of P2O5, from 86 mol % to 88 mol % of P2O5, from 88 mol % to 89 mol % of P2O5, from 89 mol % to 90 mol % of P2O5, from 90 mol % to 91 mol % of P2O5, from 91 mol % to 92 mol % of P2O5, from 92 mol % to 94 mol % of P2O5, or from 94 mol % to 95 mol % of P2O5 with respect to the phosphate glass matrix; and the phosphate glass matrix has a glass melting temperature that is at least 400° C. and no greater than 600° C.

7. The device of claim 1, wherein:

the network-forming component comprises at least 45 mol % and no greater than 55 mol % of $P_2O_5$ with respect to the phosphate glass matrix.

8. The device of claim 1, wherein the modifier further comprises at least 0.1 mol % and no greater than 5 mol % of with respect to the phosphate glass matrix.

9. The device of claim 1, wherein the modifier further comprises:

at least 15 mol % and no greater than 30 mol % of $Na_2O$ with respect to the phosphate glass matrix; and at least 15 mol % and no greater than 30 mol % of $K_2O$ with respect to the phosphate glass matrix.

10. The device of claim 1, further comprising a volume of storage medium within which the phosphate glass matrix is submerged, wherein the storage medium includes one or more members selected from a group consisting of a neat nonaqueous solvent including neat ethanol.

11. The device of claim 1, wherein the modifier further comprises at least 0.1 mol % and no greater than 5 mol % of TiO2, at least 0.1 mol % and no greater than 5 mol % of SiO2, at least 0.1 mol % and no greater than 5 mol % of B2O3, at least 15 mol % and no greater than 30 mol % of Na2O, at least 15 mol % and no greater than 30 mol % of K2O.

12. The device of claim 1, wherein the tubular shape includes one or more structural features selected from a group consisting of a smooth outer surface, a smooth edge, and a tapered end, wherein the one or more structural features are configured for insertion into and anastomosis of at least a blood vessel.

13. The device of claim 12, wherein the device is configured to form substantially no shards during its dissolution.

14. The device of claim 1, wherein the device is manufactured from a glass melt in a silica crucible.

15. The device of claim 14, wherein the glass melt is prepared from a mixture of precursors, the mixture including one or more members selected from a group consisting of $(NH_4)_3PO_4$, $CaCO_3$, and $Na_2HPO_4$.

16. A method of manufacturing a self-dissolving device for microvascular anastomosis, the method comprising:

preparing a glass melt in a silica crucible;

injecting a gas bubble into the glass melt;

shaping the glass melt containing the gas bubble into a phosphate glass structure having a tubular shape;

cooling the phosphate glass structure, wherein the phosphate glass structure comprises a network-forming component and a modifier; and truncating the phosphate glass structure into a desired length to form a phosphate glass matrix comprising:

a network-forming component; and a modifier, wherein the modifier comprises at most 15 mol % of CaO and does not include MgO with respect to the phosphate glass matrix, wherein:

the phosphate glass matrix has a glass melting temperature that is at least 1,000° C. and no greater than 1,200° C.; and the device has a dissolution time ranging from 2 minutes to 30 minutes.

17. The method of claim 16, wherein preparing the glass melt comprises preparing the glass melt from a mixture of precursors, the mixture including one or more members selected from a group consisting of $(NH_4)_3PO_4$, $CaCO_3$, and $Na_2HPO_4$.

18. The method of claim 16, wherein shaping the glass melt comprises extruding the glass melt using an extruder.

19. The method of claim 16, wherein the tubular shape has an outer diameter that is within an inclusive range of one or more of 1-5 mm, 2-4 mm, 3.3-3.8 mm, and 1-10 cm.

20. The method of claim 16, wherein the tubular shape has an outer diameter-to-thickness ratio that is within an inclusive range of one or more of 3-10 and 4.5-5.5 and a dissolution rate of the device is selected as a function of the outer diameter-to-thickness ratio based on the dissolution time.

21. The method of claim 16, wherein shaping the glass melt comprises shaping the glass melt into a tubular shape to create one or more structural features selected from a group consisting of a smooth outer surface, a smooth edge, and a tapered end.

22. The method of claim 16, wherein the desired length is at least 5 millimeters and no greater than 20 millimeters.

23. The method of claim 16, wherein the device has a dissolution time that is at least 2 minutes and no greater than 30 minutes.

24. The method of claim 16, wherein:

the network-forming component comprises a mol % of P2O5 with respect to the phosphate glass matrix within an inclusive range consisting of one or more of from 82 mol % to 84 mol % of P2O5, from 84 mol % to 86 mol % of P2O5, from 86 mol % to 88 mol % of P2O5, from 88 mol % to 89 mol % of P2O5, from 89 mol % to 90 mol % of P2O5, from 90 mol % to 91 mol % of P2O5, from 91 mol % to 92 mol % of P2O5, from 92 mol % to 94 mol % of P2O5, or from 94 mol % to 95 mol % of P2O5 with respect to the phosphate glass structure; and the phosphate glass structure has a glass melting temperature between 400° C. and 600° C.

25. The method of claim 16, wherein:

the network-forming component comprises at least 45 mol % and no greater than 55 mol % of $P_2O_5$ with respect to the phosphate glass structure.

26. The method of claim 16, wherein the modifier comprises:

at least 15 mol % and no greater than 30 mol % of $Na_2O$ with respect to the phosphate glass structure; and at least 15 mol % and no greater than 30 mol % of $K_2O$ with respect to the phosphate glass structure.

27. The method of claim 16, wherein the modifier comprises at least 0.1 mol % and no greater than 5 mol % of with respect to the phosphate glass structure.

28. The method of claim 16, further comprising submerging the device in a volume of storage medium, wherein the storage medium includes one or more members selected from a group consisting of a neat nonpolar solvent including neat ethanol.

29. The method of claim 16, wherein the device is configured to dissolve into physiological ions with negligible cytotoxic effects.

30. The method of claim 29, wherein the device is configured to form substantially no shards during its dissolution.

31. A self-dissolving device for microvascular anastomosis, the device comprising:

a phosphate glass matrix having a tubular shape, the phosphate glass matrix comprising:

a network-forming component; and a modifier, wherein the modifier comprises at most 15 mol % of CaO and does not include MgO with respect to the phosphate glass matrix, wherein:

the phosphate glass matrix has a glass melting temperature that is at least 400° C. and no greater than 600° C.; and the device has a dissolution time ranging from 2 minutes to 30 minutes, wherein the tubular shape has an outer diameter 1-10 cm and outer diameter-to-thickness ratio of 3-10 for intestinal implementation.

* * * * *